(12) United States Patent
Pulé et al.

(10) Patent No.: US 11,643,453 B2
(45) Date of Patent: May 9, 2023

(54) CELL

(71) Applicant: AUTOLUS LIMITED, London (GB)

(72) Inventors: Martin Pulé, London (GB); James Sillibourne, London (GB); Lukas Stanczuk, London (GB)

(73) Assignee: AUTOLUS LIMITED, London (GB)

(*) Notice: Subject to any disclaimer, the term of this patent is extended or adjusted under 35 U.S.C. 154(b) by 458 days.

(21) Appl. No.: 16/754,673

(22) PCT Filed: Oct. 12, 2018

(86) PCT No.: PCT/GB2018/052931
§ 371 (c)(1),
(2) Date: Apr. 8, 2020

(87) PCT Pub. No.: WO2019/073248
PCT Pub. Date: Apr. 18, 2019

(65) Prior Publication Data
US 2020/0255494 A1  Aug. 13, 2020

(30) Foreign Application Priority Data
Oct. 12, 2017 (GB) .................................. 1716728

(51) Int. Cl.
*A61K 35/17* (2015.01)
*C07K 14/74* (2006.01)
*C12N 5/0783* (2010.01)
*A61K 39/00* (2006.01)

(52) U.S. Cl.
CPC ........ *C07K 14/70539* (2013.01); *A61K 35/17* (2013.01); *A61K 39/0011* (2013.01); *C12N 5/0636* (2013.01); *A61K 2039/5156* (2013.01); *C07K 2319/02* (2013.01); *C12N 2510/00* (2013.01)

(58) Field of Classification Search
None
See application file for complete search history.

(56) References Cited

U.S. PATENT DOCUMENTS

| 7,052,906 B1 | 5/2006 | Lawson et al. |
| 7,381,803 B1 | 6/2008 | Weiner et al. |
| 2018/0362975 A1* | 12/2018 | Chen .................... C12N 15/113 |
| 2020/0255494 A1 | 8/2020 | Pulé et al. |

FOREIGN PATENT DOCUMENTS

| WO | WO-2005/023299 A2 | 3/2005 |
| WO | WO-2013/153391 A1 | 10/2013 |
| WO | WO-2015/052538 A1 | 4/2015 |
| WO | WO-2016/135470 A1 | 9/2016 |
| WO | WO-2016/166521 A1 | 10/2016 |
| WO | WO-2016/193696 A1 | 12/2016 |
| WO | WO-2017/029512 A1 | 2/2017 |
| WO | WO-2018/096361 A1 | 5/2018 |
| WO | WO-2019/073248 A1 | 4/2019 |
| WO | WO-2020/208346 A1 | 10/2020 |

OTHER PUBLICATIONS

Pyzik et al. FcRn: The Architect Behind the Immune and Nonimmune Functions of IgG and Albumin. The J. of Immunology, 2015, 194: 4595-4603.*
Jena et al. Redirecting T-cell specificity by introducing a tumor-specific chimeric antigen receptor. Blood, 2010, 116: 1035-1044.*
Tscherning et al. Signal Transduction via MHC Class-I Molecules in T cells. Scancf. J. Immunol. 39. 117 121. 1994.*
Fishman et al., "Adoptive Transfer of mRNA-Transfected T Cells Redirected against Diabetogenic CD8 T Cells can Prevent Diabetes," Molecular Therapy, 25(2):456-464 (2017).
Brodsky et al., "Characterization of a monoclonal anti-β2-microglobulin antibody and its use in the genetic and biochemical analysis of major histocompatibility antigens," Eur. J. Immunol. 9:536-545 (1979).
Chen et al., "Fusion Protein Linkers: Property, Design and Functionality," Adv Drug Deliv Rev. 65(10:1357-1369 (2013).
Donnelly et al., "The 'cleavage' activities of foot-and-mouth disease virus 2A site-directed mutants and naturally occurring '2A-like' sequences," J. Gen. Virol. 82:1027-1041 (2001).
International Search Report and Written Opinion from International Application No. PCT/GB2018/052931 dated Jan. 9, 2019.
Margalit et al., "Chimeric β2 microglobulin/CD3 polypeptides expressed in T cells convert MHC class I peptide ligands into T cell activation receptors: a potental too for specific targeting of pathogenic $CD8^+$ T cells," International Immunology 15(11):1379-1387 (2003).
Mhashilkar et al., "Intrabody-mediated phenotypic knockout of major histocompatibility complex class I expression in human and monkey cell lines and in primary human keratinocytes," Gene Ther.995:207-319 (2002).
Parham et al., "Arginine 45 Is a Major Part of the Antigenic Determinant of Human $β_2$-Microglobulin Recognized by Mouse Monoclonal Antibody BBM.1," J. Biol. Chem. 258:6179-6186 (1983).
Ren et al., "Multiplex Genome Editing to Generate Universal CAR T Cells Resistant to PD1 Inhibition," Clinical Cancer Research 23(9):2255-2266 (2016).
Andris et al., "The Human Antibody Repertoire: Heavy and Light Chain Variable Region Gene Usage in Six Alloantibodies Specific for Human HLA Class I and Class II Alloantigens," Molecular Immunology, 32(14/15):1105-1122 (1995).
Devine et al., "Orientation of the Ig Domains of CD8?? Relative to MHC Class I," Journal of Immunology 162:846-851 (1999).

(Continued)

*Primary Examiner* — Nianxiang Zou
(74) *Attorney, Agent, or Firm* — Marshall, Gerstein & Borun LLP

(57) ABSTRACT

The present invention provides a cell which comprises; (i) a chimeric antigen receptor (CAR) or a transgenic T-cell receptor (TCR); and (ii) a polypeptide capable of co-localizing a beta-2 microglobulin component of a MHC class I molecule with an intracellular signalling domain within the cell.

13 Claims, 7 Drawing Sheets
Specification includes a Sequence Listing.

(56) References Cited

OTHER PUBLICATIONS

International Search Report and Written Opinion for International Application No. PCT/GB2020/050908, dated Jul. 14, 2020, 12 Pages.

Jin J et al., "Development of an Allogeneic NKT Cell Platform for Off-the-Shelf Cancer Immunotherapy," Molecular Therapy 26(5S1):173, Embase, Elsevier Science Publishers, Amsterdam, NL, Database accession No. EMB-623339459, XP002796558, May 1, 2018.

Jin L., et al., "MHC Class II Structural Requirements for the Association with Ig?/?, and Signaling of Calcium Mobilization and Cell Death," Immunology Letters, 116:184-194 (2008).

Lang P., et al., "TCR-Induced Transmembrane Signaling by Peptide/MHC Class II via Associated Ig-?/? Dimers," Science, 291:1537-1540 (2001).

Lefranc M.P., et al., "IMGT, The International ImMunoGeneTics Database," Nucleic Acids Res, 27 (1):209-212 (1999).

Mo F., et al., "Rejection-Resistant Off-the-Shelf T Cells for Adoptive Cell Therapy", Biology of Blood and Marrow Transplantation, vol. 25(3), Abstract, p. S168 (2019).

Quach D.H., et al., "Engineering Therapeutic T-Cells to Recognize and Target Mismatched Alloreactive Human T-Cells", Molecular Therapy 25(5S1), pp. 88, Abstract (2017).

Wang X.X., et al., "Affinity Maturation of Human CD4 by Yeast Surface Display and Crystal Structure of a CD4-HLA-DR1 Complex," PNAS, 108(38):15960-15965 (2011).

Watkins N.A., et al., "The Isolation and Characterisation of Human Monoclonal HLA-A2 Antibodies from an Immune V Gene Phage Display Library," Tissue Antigens, 55(3):219-228 (2000).

Weissberg O., et al., "Endowing Human CD8 T Cells With a Veto-Like Recognition Capacity via the Electroporation of MHC-I/CD3[Zeta] mRNA," Transplant Immunology, 55:101202, Mar. 20, 2019, 5 pages.

\* cited by examiner

CELL

CROSS-REFERENCE TO RELATED APPLICATIONS

This is a U.S. National Phase of International Application No. PCT/GB2018/052931, filed Oct. 12, 2018, which claims priority to Great Britain Application No. 1716728.9, filed Oct. 12, 2017.

FIELD OF THE INVENTION

The present invention relates to a cell which expresses a chimeric antigen receptor (CAR) or a T-cell receptor (TCR); and in particular to approaches to control immune rejection of such cells in a recipient.

BACKGROUND TO THE INVENTION

After infusion, CAR T-cells engraft within the recipient and proliferate after encountering target bearing cells. CAR T-cells then persist and their population slowly contracts over time. CAR T-cell persistence can be determined in clinical studies by real-time PCR for the transgene in blood samples or by flow-cytometry for the CAR in blood samples and clinical researchers have found a correlation between persistence and sustained responses. This correlation is particularly pronounced in CD19 CAR therapy of B-Acute lymphoblastic leukaemia (ALL). Often in this setting, loss of CAR T-cell engraftment heralds relapse of the leukaemia.

CAR T-cells can result in activation of a cellular mediated immune response which can trigger rejection of the CAR T-cells. This is due to immunogenicity of the components engineered into the cell either through non-self proteins or through non-self sequences formed from junctions between self-proteins used to make receptors and other engineering components.

CARs are artificial proteins which are typically composed of a targeting domain, a spacer domain, a transmembrane domain and a signaling domain. The targeting domain is typically derived from an scFv which may be murine. While this scFv can be human or humanized and other components individually are derived from self-proteins, the junctions between them can still be immunogenic. For instance, within the scFv there are junctions between the heavy chain and the linker and the linker and the light chain. There is then a junction between the scFv and the spacer domain. If the transmembrane domain is not continuous with the spacer there is a further junction there. Similarly, if the transmembrane domain is not continuous with the amino-terminal portion of the endodomain, there is a further junction there. Finally, most endodomains have at least two components and sometimes more with junctions subsequently between each component.

In addition, CAR T-cells are often engineered with further components. These components include suicide genes (e.g. the HSV-TK enzyme). This enzyme was found to be highly immunogenic and caused a cellular immune depletion of CAR T-cells outside of the context of the profound immunosuppression of haploidentical haematopoietic stem cell transplantation. Other less immunogenic suicide genes may still provide some immunogenicity, as almost every kind of engineered component which involves a fusion between two proteins or use of a xenogeneic protein can be immunogenic.

In many settings, CAR T-cells are generated from autologous T-cells. In this setting, allo-responses do not occur. In some circumstances, T-cells from an allogeneic donor are used. This can occur if for instance the patient has had an allogeneic haematopoietic stem cell transplant. In this case, harvested T-cells will be allogeneic. Otherwise, a patient may have insufficient T-cells to generate a CAR T-cell product due to chemotherapy induced lymphopenia.

Rejection of allogeneic cells can be due to minor mismatch or major mismatch. Minor mismatch occurs in the setting where allogeneic T-cells are human leukocyte antigen (HLA)-matched to the recipient. In this case, rejection occurs due to minor histocompatibility antigens which are non-HLA differences between individuals which result in presentation of non-self (donor) epitopes/immunogenic peptides on HLA. In the case where donor and recipient are mismatched, or are only partially matched. T-cell receptors (TCR) on endogenous T-cells of a recipient can interact in a non-specific way with a mismatched HLA and cause rejection consequently. Both minor and major forms of allogeneic rejection are caused by HLA interacting with TCR.

One method for preventing rejection by cellular immune responses is by genomic editing tools such as engineered zinc finger nucleases, TALENs, CrispR/Casp9, MegaTALs and meganucleases. Using such tools elements of peptide/HLA presentation can be disrupted. The most direct way of doing this is by disrupting HLA expression. This can be achieved by disruption of the HLA locus or alternatively by disruption of the beta-2 microglobulin (B2M) locus (which then stops MHC class I expression). Other approaches include disrupting of components of peptide presentation.

Another method of preventing cellular mediated immune rejection relies on protein based approaches to disrupt HLA expression. For instance, an antibody single-chain variable fragment which recognizes B2M and which has a Golgi/ER retention signal at its carboxy terminus can result in down-regulation of HLA since B2M is retained within the ER/Golgi complex. Other approaches include using viral proteins which have evolved to disrupt HLA expression and function.

The main limitation of all these approaches is they rely on or result in surface down-regulation of class I which in turn triggers rejection by NK cells. Hence these approaches solve one problem of alpha/beta T-cell mediated cellular rejection but cause another type of cellular immune-rejection, namely that by NK cells.

One further method has been described—that of rendering the engineered T-cells resistant to a potent immunosuppressive agent and administering said immunsuppressive agent after administration of engineered T-cells. This approach is limited since it causes profound immunosuppression in the recipient since all normal T-cells are suppressed rather than just the ones which can reject the engineered cell product.

There is therefore a need for alternative approaches to reduce cellular mediated immune rejection of engineered cells, in particular engineered immune cells expressing a CAR or an engineered-TCR.

SUMMARY OF ASPECTS OF THE INVENTION

The present inventors have found that it is possible to couple the binding of a MHC class I on a first cell to a TCR on a second cell to induce—directly or indirectly—signalling in the first cell. Notably, the present MHC class I signalling systems are capable of presenting the same range of peptides as a corresponding endogenous MHC class I molecule. As such, any peptide which is naturally presented by MHC class I is presented by the MHC class I of the present invention. This includes any xenogeneic or junctional peptides that may be immunogenic. In an allogeneic setting, this may also include minor histocompatibility antigens. Thus an MHC class I as defined herein will interact with any endogenous, reactive T-cells present in the recipient of an engineered cell of the present invention through recognition of peptide/MHC complexes. The reactive T-cell can thus be depleted by activation of cytotoxic-mediated cell killing by the cell of the present invention. Hence, a cellular immune response against the cell of the present invention can be reduced.

Thus, in a first aspect the present invention provides a cell which comprises;
(i) a chimeric antigen receptor (CAR) or a transgenic T-cell receptor (TCR); and
(ii) a polypeptide capable of co-localizing a beta-2 microglobulin component of a MHC class I molecule with an intracellular signalling domain within the cell.

The polypeptide capable of co-localizing the beta-2 microglobulin component of the MHC class I molecule with the intracellular signalling domain may be an engineered beta-2 microglobulin further comprising an endodomain comprising an intracellular signalling domain.

The engineered beta-2 microglobulin may further comprise a transmembrane domain between the beta-2 microglobulin and the endodomain comprising an intracellular signalling domain.

The polypeptide capable of co-localizing the beta-2 microglobulin component of the MHC class I molecule with the intracellular signalling domain may be a beta-2 microglobulin polypeptide linked to a component of the TCR complex, suitably the beta-2 microglobulin polypeptide may be linked to a component of the CD3 complex.

The component of the CD3 complex may be selected from CD3-zeta, CD3-epsilon, CD3-gamma or CD3-delta. The beta-2 microglobulin polypeptide may fused to the component of the CD3 complex by a linker peptide. The beta-2 microglobulin polypeptide may be linked to the ectodomain of a component of the CD3 complex.

The polypeptide capable of co-localizing the beta-2 microglobulin component of the MHC class I molecule with the intracellular signalling domain may be a bispecific polypeptide which comprises; (i) a first binding domain which is capable of binding to the beta-2 microglobulin polypeptide and (ii) a second binding domain which is capable of binding to a polypeptide comprising an intracellular signalling domain or a component of the CD3 complex.

The bispecific molecule may be membrane-tethered.

The intracellular signalling domain may comprise an immunoreceptor tyrosine-based activation (ITAM) motif.

The intracellular signalling domain may be an intracellular T-cell signalling domain which comprises one or more of the following: CD3 zeta endodomain, CD28 endodomain, OX40 endodomain, 4-1BB endodomain, CD2 endodomain, CD27 endodomain, ICOS endodomain, CD40 endodomain.

The intracellular T-cell signalling domain may comprise the CD3 zeta endodomain.

The cell may be an alpha-beta T cell, a NK cell, a gamma-delta T cell, or a cytokine induced killer cell.

In a further aspect, the present invention provides a nucleic acid construct which comprises:
(i) a first nucleic acid sequence which encodes a chimeric antigen receptor (CAR) or a transgenic TCR; and
(ii) a second nucleic acid sequence which encodes a polypeptide capable of co-localizing a beta-2 microglobulin component of a MHC class I molecule with an intracellular signalling domain according to the present invention.

The first and second nucleic acid sequences may be separated by a co-expression site.

In another aspect the present invention provides a kit of nucleic acid sequences comprising:
(i) a first nucleic acid sequence which encodes a chimeric antigen receptor (CAR) or a transgenic TCR; and
(ii) a second nucleic acid sequence which encodes a polypeptide capable of co-localizing a beta-2 microglobulin component of a MHC class I molecule with an intracellular signalling domain according to the present invention.

In a further aspect, the present invention provides a vector which comprises a nucleic acid construct of the present invention.

In another aspect the present invention provides a kit of vectors which comprises:
(i) a first vector which comprises a nucleic acid sequence which encodes a chimeric antigen receptor (CAR) or a transgenic TCR; and
(ii) a second vector which comprises a nucleic acid sequence which encodes a polypeptide capable of co-localizing a beta-2 microglobulin component of a MHC class I molecule with an intracellular signalling domain according to the present invention.

The present invention further provides a pharmaceutical composition which comprises a plurality of cells; a nucleic acid construct; a first nucleic acid sequence and a second nucleic acid sequence; a vector or a first and a second vector of the present invention.

The present invention also provides a cells a nucleic acid construct; a first nucleic acid sequence and a second nucleic acid sequence; a vector; a first and a second vector; or a pharmaceutical composition of the invention for use in treating and/or preventing a disease.

The invention further provides a method for treating and/or preventing a disease, which comprises the step of administering a pharmaceutical composition of the present invention to a subject in need thereof.

The method may comprise the following steps:
(i) isolation of a cell containing sample;
(ii) transduction or transfection of the cell with a nucleic acid construct, a vector or a first and a second vector of the present invention; and
(iii) administering the cells from (ii) to a subject.

The cell isolated in part (i) of the method may be autologous. The cell isolated in part (i) of the method may be allogenic.

In a further aspect the present invention provides the use of a pharmaceutical composition of the present invention in the manufacture of a medicament for the treatment and/or prevention of a disease.

The disease may be immune rejection of the cell which comprises (i) a chimeric antigen receptor (CAR) or a transgenic TCR; and (ii) a polypeptide capable of co-localizing a beta-2 microglobulin component of a MHC class I molecule with an intracellular signalling domain.

The present invention further provides a method for making a cell according to the first aspect of the invention, which comprises the step of introducing: a nucleic acid construct, a first nucleic acid sequence and a second nucleic acid sequence; a vector or a first and a second vector of the present invention into the cell.

The cell may be from a sample isolated from a subject.

In a further aspect the present invention provides an engineered polypeptide comprising a beta-2 microglobulin component of a MHC class I molecule linked to a component of the CD3 complex.

In another aspect the present invention provides a bispecific polypeptide which comprises; (i) a first binding domain which is capable of binding to the beta-2 microglobulin polypeptide; and (ii) a second binding domain which is capable of binding to a polypeptide comprising an intracellular signalling domain or a component of the CD3 complex.

In a further aspect, the present invention provides a method for deleting or eliminating T cells in vivo which recognise a peptide presented by the MHC class I molecule of a cell according to the first aspect of the invention, which comprises the step of administration of a cell according to the first aspect of the invention to a subject, such that T cells in the subject which recognise such a peptide/MHC are deleted by negative selection.

The method may delete T cells which recognise a peptide derived from an exogenous protein expressed by the cell of the invention. An "exogenous" protein is a protein which the cell has been engineered to express, for example by recombinant means. It is a protein not normally expressed by the cell.

The method may delete T cells which recognise a peptide derived from a chimeric antigen receptor (CAR), a transgenic T-cell receptor (TCR), a suicide gene, a chimeric cytokine receptor or a signal transduction modifying protein expressed by the cell of the invention.

The method may delete T cells which recognise a peptide derived from a chimeric antigen receptor (CAR) expressed by the cell of the invention.

In a further aspect there is provided a method for preventing immune rejection of a cell of the first aspect of the invention, which comprises the step of deleting T cells in vivo which recognise a peptide presented by the MHC class I molecule of the cell by a method as described above.

Major Histocompatibility Complex (MHC) Class I CAR is a heterodimer composed of two non-covalently linked polypeptide chains, α and β2-microglobulin (βm). The α1 and α2 subunits together with a loaded peptide bind to a T-cell receptor (TCR) expressed on the surface of T cells. β2-microglobulin is connected to a transmembrane domain which anchors the molecule in the cell membrane and is further linked to an endodomain which acts to transmit intracellular signals to the cell. The endodomain can be composed of one or more signalling domains.

Figure 5:
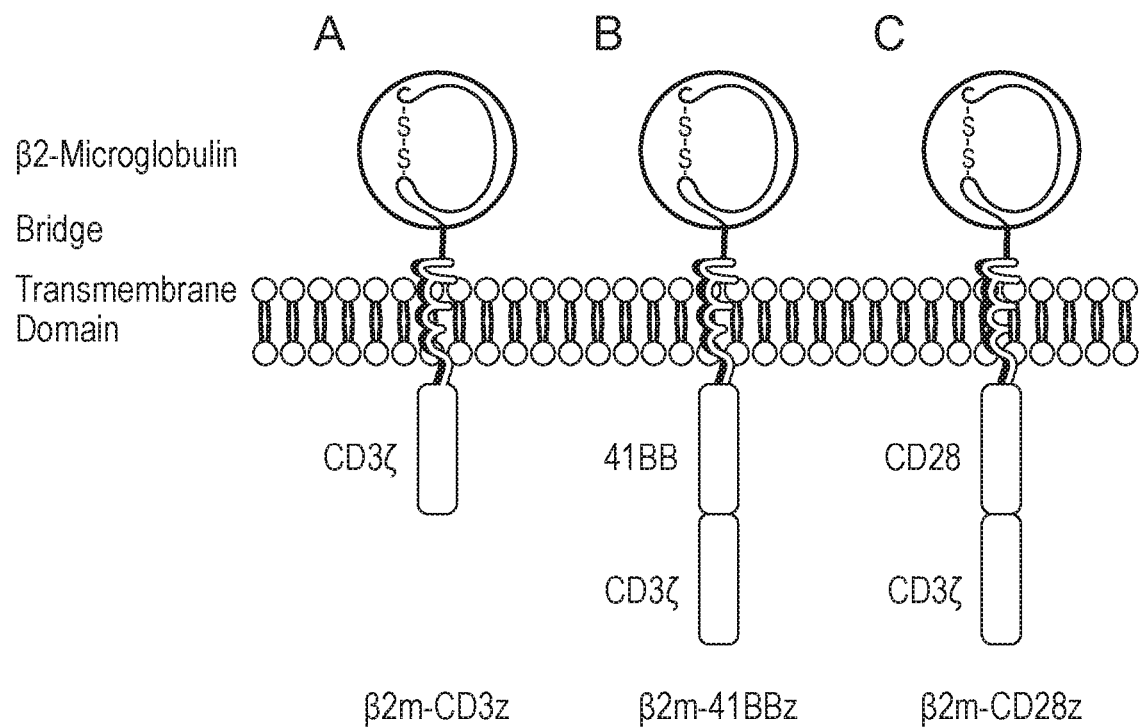

FIG. 5—Schematic diagram illustrating three possible β2m-based CAR designs

In the first CAR (A) β2-microglobulin is linked via a bridge to the CD3 ζ transmembrane domain which is then linked to the CD3 ζ endodomain. Two other CAR designs (B and C) have added co-stimulatory domains, 41BB or CD28 respectively.

Figure 6:
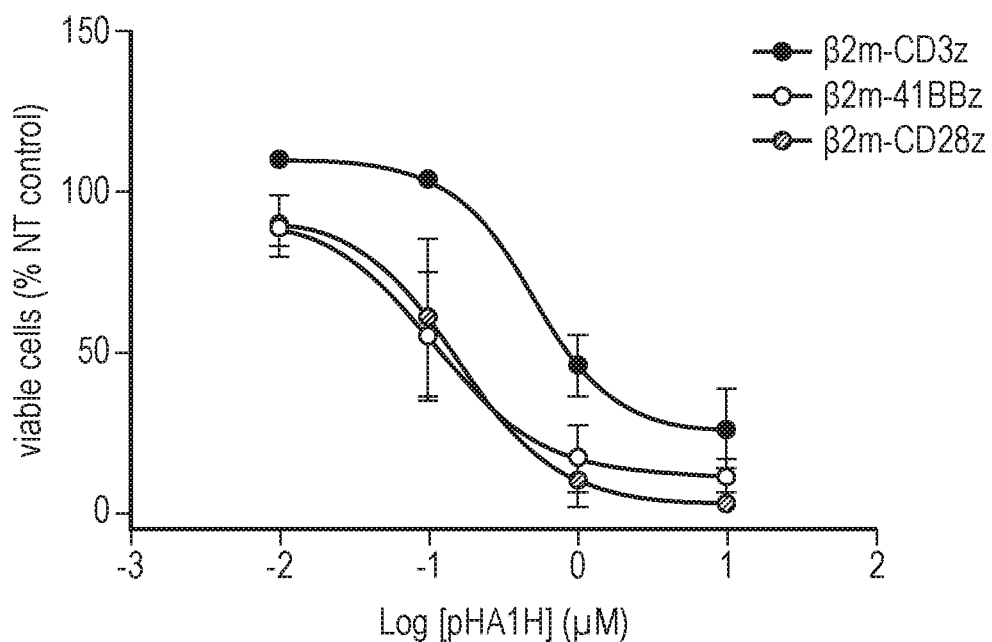

FIG. 6—MHC I CAR-T cells can kill target T cells via MHC I/TCR interaction

Three β2m constructs (β2m-CD3z, β2m-41BBz and β2m-CD28z) were used to transduce PBMCs from two healthy donors of HLA-A02 haplotype. Recombinant HA1H peptide which naturally binds to HLA-A02 was used to pulse CAR-T cells at a range of concentrations (top concentration=10 μM). Pulsed CAR-T cells were co-cultured with SupT1 cells expressing anti-HA1H TCR at 2:1 effector to target ratio. Following a 48 h incubation, the number of viable SupT1 target cells was assessed by flow cytometry and normalised to non-transduced (NT) control. All three β2m constructs were effective at killing target cells. EC50 for HA1H peptide ranged from ~0.5 μM (β2m-CD3z) to ~0.1 μM (β2m-41BBz).

Figure 7:
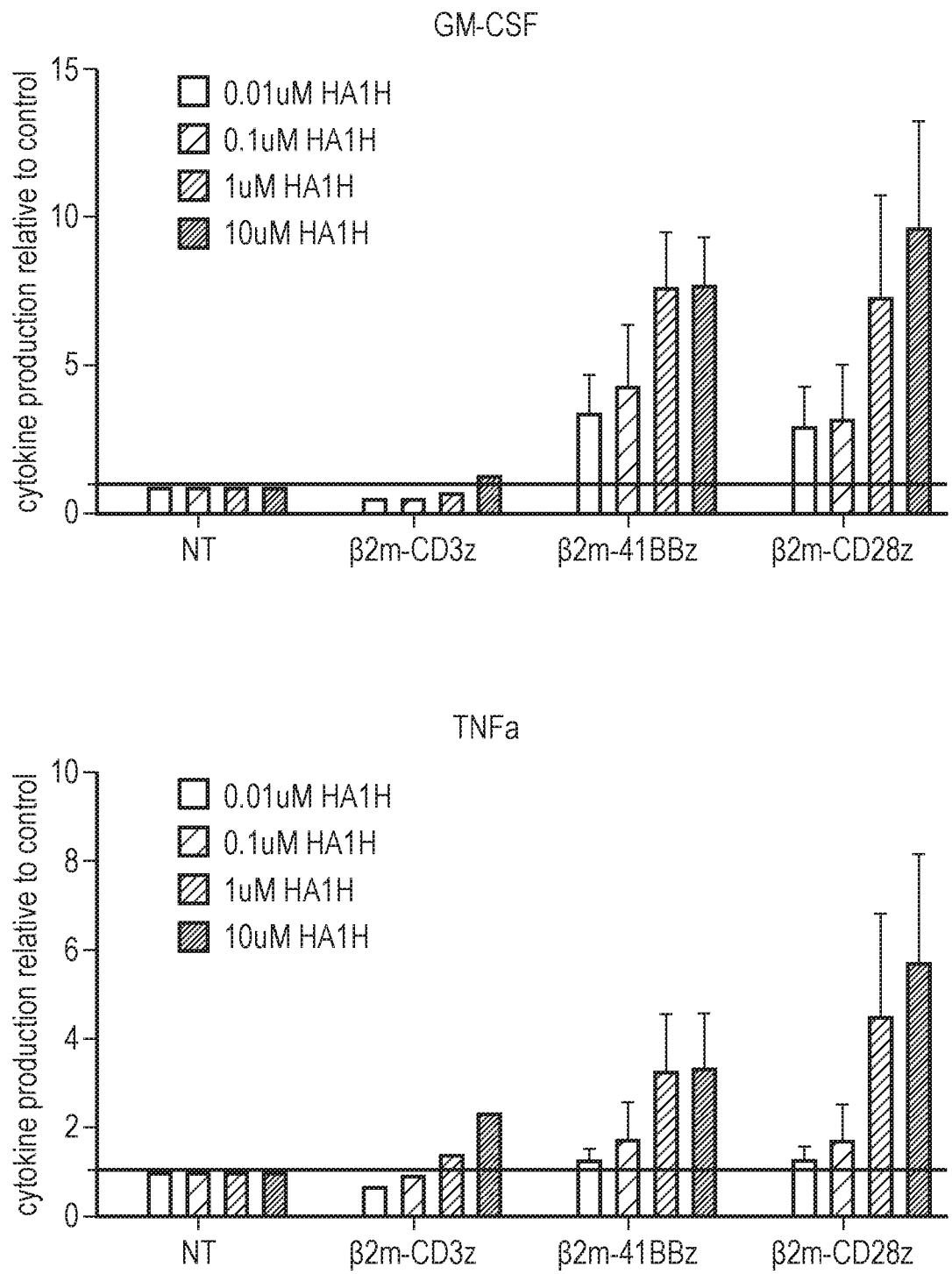
Figure 7:
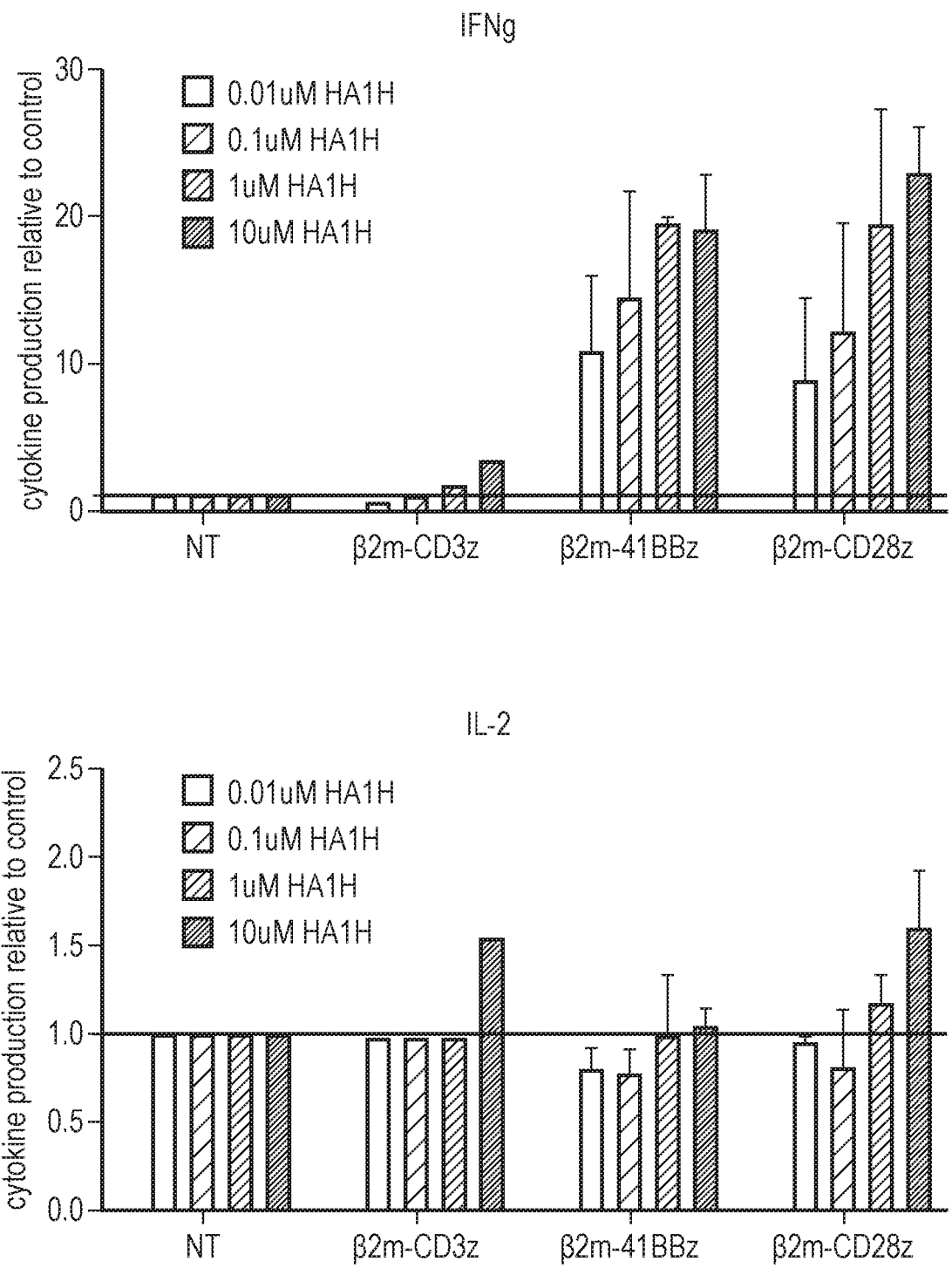

FIG. 7—Engagement of MHC I CAR-T cells with target cells results in production of cytokines Relative cytokine concentration in the media from a 48h co-culture of MHC I CAR-T cells (β2m-CD3z n=1; β2m-41BBz and β2m-CD28z n=2) and SupT1.HA1H-TCR target cells at 2:1 effector to target ratio. CAR-T cells were pulsed with a recombinant HA1H peptide at a range of concentrations prior to seeding with the targets. NT control was used to normalise the cytokine concentrations. The Red line indicates the level of cytokines produced by NT control.

DETAILED DESCRIPTION OF THE INVENTION

Co-Localizing B2M with an Intracellular Signalling Domain

The present invention provides a cell which comprises; (i) a chimeric antigen receptor (CAR) or a transgenic T-cell receptor (TCR); and (ii) a polypeptide capable of co-localizing a beta-2 microglobulin component of a MHC class I molecule with an intracellular signalling domain within the cell.

Neo-epitopes or allo-antigens are presented on MHC class I molecules. MHC class I is formed by assembly of beta-2-microglobulin (B2M) with a MHC class I protein which has been loaded with a peptide. While MHC class I proteins are highly polymorphic, B2M is conserved.

Figure 1:
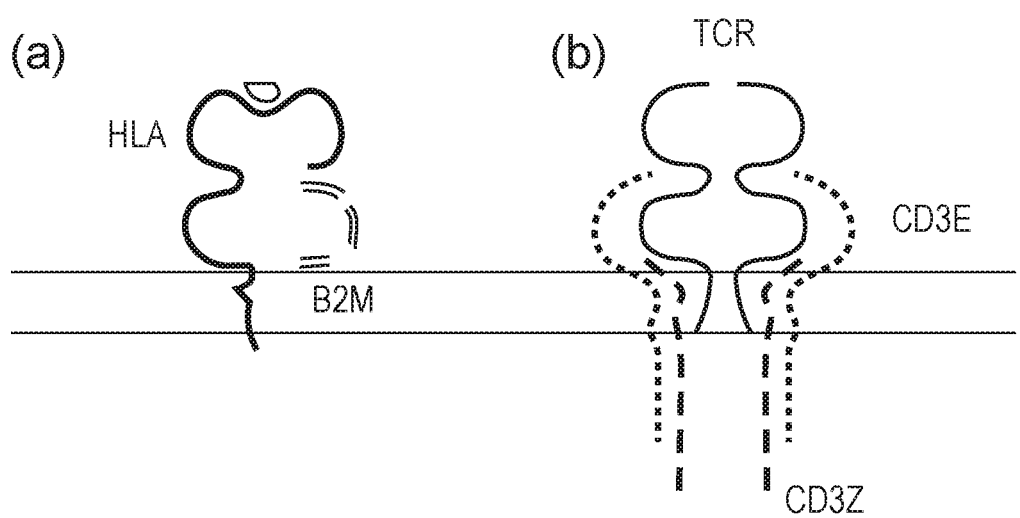
FIG. 1—(a) MHC class I molecular complex which is composed of MHC and B2M; (b) The TCR complex which is composed of TCRalpha/beta chains surrounded by CD3 elements FIG. 2—(a) B2M-Z construct: The B2M construct is fused in frame to a transmembrane domain and CD3-zeta endodomain; (b) B2M-TCR bispecific construct: a scFv which recognizes B2M is fused with a linker to a second scFv which recognizes the CD3/TCR complex. This is then anchored to the membrane via a transmembrane domain; (c) Fusion between B2M and CD3/TCR: As an example, a fusion between B2M via a flexible linker to CD3 Epsilon is shown.

The MHC class I molecule is comprised of 4 immunoglobulin-like loops. The MHC protein provides three loops (α1, α2 and α3). A separate protein, B2M, provides the fourth loop (see FIG. 1(a)). B2M lies beside the α3 chain of the MHC class I on the cell surface. Unlike α3, endogenous B2M has no transmembrane region. Directly above B2M (that is, further away from the cell) lies the a1 chain, which itself is next to the α2.

An illustrative B2M amino acid sequence is shown as SEQ ID NO: 1:

```
                                          SEQ ID NO: 1
MSRSVALAVLALLSLSGLEAIQRTPKIQVYSRHPAENGKSNFLNCYVSGF
HPSDIEVDLLKNGERIEKVEHSDLSFSKDWSFYLLYYTEFTPTEKDEYAC
RVNHVTLSQPKIVKWDRDM
```

A B2M polypeptide sequence for use in the present invention may comprise the sequence shown as SEQ ID NO: 1 or a variant thereof having at least 80% sequence identity.

The variant maintains ability to assemble with a MHC class I protein and facilitate productive peptide presentation by the MHC class I complex.

The variant of SEQ ID NO: 1 may have at least 80, 85, 90, 95, 98 or 99% sequence identity, provided that the variant sequence retains the capacity to assemble with a MHC class I protein and facilitate productive peptide presentation by the MHC class I complex.

The percentage identity between two polypeptide sequences may be readily determined by programs such as BLAST, which is freely available at http://blast.ncbi.nlm.nih.gov. Suitably, the percentage identity is determined across the entirety of the reference and/or the query sequence.

As used herein, "capable of co-localizing a B2M component of a MHC class I molecule with an intracellular signalling domain within the cell" means that, when a TCR on a reactive T-cell binds to a peptide/MHC complex on a cell of the present invention, the polypeptide co-localizes the B2M component with the intracellular signalling domain such that the intracellular signalling domain transmits an activating signal in the cell of the present invention.

Suitably, the activating signal that is induced stimulates the cell of the present invention to deplete the reactive T cell which recognises the peptide/MHC complex. Such depletion is typically achieved by cell-mediated, cytotoxic killing mechanisms.

Suitable methods for determining activation of the cytotoxic killing mechanisms in a cell include, but are not limited to, chromium release assays, flow-cytometry based killing assays, measuring cytokine release after effector and target encounter (e.g. by ELISA or cytokine bead array), demonstration of de-granulation or activation on effector cells after effector-target cell encounter by flow-cytometery.

Engineered B2M

In some embodiments, the polypeptide capable of co-localizing the B2M component of the MHC class I molecule with an intracellular signalling domain is an engineered B2M further comprising an endodomain comprising an intracellular signalling domain.

Such an engineered B2M component comprises a B2M polypeptide and is capable of assembling with a MHC class I protein to facilitate productive peptide presentation by the MHC class I complex. In addition, the engineered B2M further comprises an intracellular signalling domain that is capable of transmitting an activating signal following binding of a TCR to the peptide/MHC complex which comprises the engineered B2M. The intracellular signalling domain may be an intracellular signalling domain as described herein.

Engineered B2M polypeptides are described in Margalit et al. (*Int. Immunol.* 15, 1379-1387 (2003)). These engineered MHC/B2M polypeptides include a peptide linked to the engineered B2M so that the MHC class I exclusively presents the linked peptide. A T-cell expressing such a construct will selectively deplete any reactive T-cell which recognizes the selected peptide/MHC complex. In this way, selective immunosuppression against a known antigen can be executed by depletion of cognate T-cells.

In contrast, any peptide which is naturally presented by MHC class I will be presented by the present MHC class I complexes. This advantageously enables a cell expressing the present MHC class I complexes to deplete endogenous, reactive T cells which recognise any peptide/MHC complex which is presented by the cell of the present invention.

The MHC class I complex of the present invention may present a peptide derived from the chimeric antigen receptor (CAR) or a transgenic T-cell receptor (TCR) expressed by the cell. Alternatively it may present a peptide derived from another non-endogenous protein which the cell is engineered to express, such as a suicide gene, chimeric cytokine receptor or signal transduction modifying protein.

A suicide-gene is a genetically encoded mechanism which allows selective destruction of adoptively transferred T-cells in the face of unacceptable toxicity. Two suicide-genes have been tested in clinical studies: Herpes Simplex Virus thymidine kinase (HSV-TK) and inducible caspase 9 (iCasp9). The cell of the invention may, for example, express one of these suicide genes or an alternative system, such as one of those described in WO2013/153391, WO2016/135470 or WO2016/166521.

Chimeric cytokine receptors provide a cytokine signal to the cell. They may be constitutively active or induced by a molecule such as a tumour secreted factor, cell membrane protein or a chemokine. Both types of chimeric cytokine receptors are described in more detail in WO2017/029512.

A signal transduction modifying protein may, for example be a truncated SHP-1 or SHP-2 molecule which comprises or both SH2 domains but lacks a phosphatase domain. Such dominant-negative SHP-1 and SHP-2 molecules compete with endogenous SHP-1 and/or SHP-2 for binding to pITIMs on inhibitory immune receptor molecules such as PD1. This reduces the de-phosphorylation of ITAM domains by SHP-1/SHP-2, thereby blocking or reducing the inhibition of immune activation mediated by these molecules. These and other signal transduction modifying proteins are described in WO2016/193696 and WO2018/096361.

Endogenous B2M polypeptides do not comprise a transmembrane domain. Suitably, the present engineered B2M further comprises a transmembrane domain located between the B2M polypeptide and the endodomain comprising an intracellular signalling domain.

The transmembrane domain may be any peptide domain that is capable of inserting into and spanning the cell membrane. A transmembrane domain may be any protein structure which is thermodynamically stable in a membrane. This is typically an alpha helix comprising of several hydrophobic residues. The transmembrane domain of any transmembrane protein can be used to supply the transmembrane portion of the invention. The presence and span of a transmembrane domain of a protein can be determined by those skilled in the art using the TMHMM algorithm (http://www.cbs.dtu.dk/services/TMHMM-2.0/). Further, given that the transmembrane domain of a protein is a relatively simple structure, i.e a polypeptide sequence predicted to form a hydrophobic alpha helix of sufficient length to span the membrane, an artificially designed TM domain may also be used (U.S. Pat. No. 7,052,906 B1 describes synthetic transmembrane components). For example, the transmembrane domain may comprise a hydrophobic alpha helix. The transmembrane domain may be derived from CD8alpha or CD28.

By way of example, the transmembrane domains of CD8alpha and CD28 are shown as SEQ ID NO: 28 and SEQ ID NO: 2, respectively.

(CD8 alpha transmembrane domain)
SEQ ID NO: 28
IYIWAPLAGTCGVLLLSLVITLY

SEQ ID NO: 2
FWVLVVVGGVLACYSLLVTVAFIIFWVR

An illustrative engineered B2M for use in the present invention is shown as SEQ ID NO: 3. This polypeptide sequence comprises a B2M domain, a transmembrane domain and an intracellular CD3-ζ endodomain.

SEQ ID NO: 3
MSRSVALAVLALLSLSGLEAIQRTPKIQVYSRHPAENGKSNFLNCYVSGFH

PSDIEVDLLKNGERIEKVEHSDLSFSKDWSFYLLYYTEFTPTEKDEYACRV

NHVTLSQPKIVKWDRDM*IYIWAPLAGTCGVLLLSLVITLYSRSADAPAYQQ*

*GQNQLYNELNLGRREEYDVLDKRRGRDPEMGGKPQRRKNPQEGLYNELQKD*

*KMAEAYSEIGMKGERRRGKGHDGLYQGLSTATKDTYDALHMQALPPR*
Bold—B2M domain
Italics—Transmembrane domain
Standard—CD3Z endodomain An engineered B2M polypeptide sequence for use in the present invention may comprise the sequence shown as SEQ ID NO: 3 or a variant thereof having at least 80% sequence identity. The variant maintains ability to assemble with a MHC class I protein, facilitate productive peptide presentation by the MHC class I complex and transmit an activating signal following binding of a TCR to the peptide/MHC complex comprising the engineered B2M.

The variant of SEQ ID NO: 3 may have at least 80, 85, 90, 95, 98 or 99% sequence identity, provided that the variant sequence retains the capacity to assemble with a MHC class I protein, facilitate productive peptide presentation by the MHC class I complex and transmit an activating signal following binding of a TCR to the peptide/MHC complex comprising the engineered B2M.

B2M/CD3 Linked Polypeptide

In other embodiments of the present invention, the polypeptide capable of co-localizing the B2M component of the MHC class I molecule with an intracellular signalling domain is a B2M polypeptide linked to a component of the TCR complex.

CD3 is a T-cell co-receptor that is involved in the activation of both cytotoxic T-cells and T-helper cells. It is formed of a protein complex composed of four distinct chains. As used herein, the term "CD3 complex" also includes the CD3 ζ-chain. In mammals, the complex contains a CD3γ chain, a CD3δ chain, and two CD3ε chains. These chains associate with the TCR to generate a TCR complex which is capable of producing an activation signal in T lymphocytes.

The CD3ζ, CD3γ, CD3δ, and CD3ε chains are highly related cell-surface proteins of the immunoglobulin superfamily containing a single extracellular immunoglobulin domain. The transmembrane region of the CD3 chains contain a number of aspartate residues are negatively charged, a characteristic that allows these chains to associate with the positively charged TCR chains. The intracellular tails of the CD3 molecules contain a single conserved motif known as an immunoreceptor tyrosine-based activation motif (ITAM), which is involved in TCR signalling.

Figure 2:
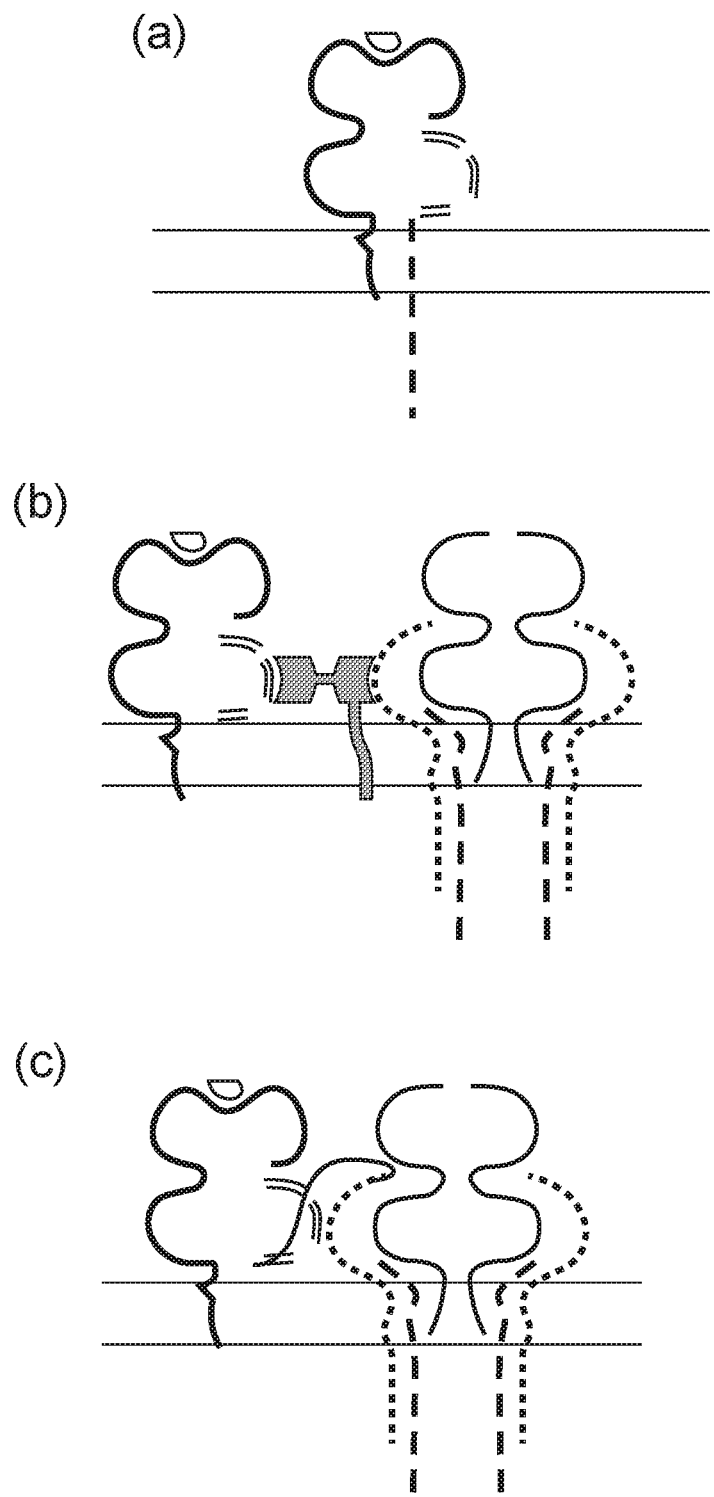

The B2M polypeptide linked to a component of the TCR complex is capable of assembling with the MHC class I complex and facilitating productive peptide presentation by the MHC class I complex. In addition, the TCR/CD3 component is able to assemble with the TCR/CD3 complex. Hence, binding of a TCR to the peptide/MHC complex comprising the B2M linked to a component of the TCR complex will trigger signalling through the CD3/TCR complex comprising the CD3 component which is linked to the B2M (see FIG. 2(c)).

The B2M polypeptide may be linked to the TCR or a component of the CD3 complex. Suitably, the B2M polypeptide may be linked to an engineered TCR polypeptide which lacks a variable domain. By way of example, the B2M polypeptide may be linked to an engineered pre-T-alpha chain. The pre-T-alpha chain is expressed on developing T cell during thymic selection and lacks a variable domain.

An illustrative sequence of an engineered pre-T-alpha chain is shown as SEQ ID NO: 30.

SEQ ID NO: 30
MAGTWLLLLLALGCPALPTGVGGTPFPSLAPPIMLLVDGKQQMVVVCLVLD

VAPPGLDSPIWFSAGNGSALDAFTYGPSPATDGTWTNLAHLSLPSEELASW

EPLVCHTGPGAEGHSRSTQPMHLSGEASTARTCPQEPLRGTPGG*ALWLGVL*

*RLLLFKLLLFDLLLT*CSCLCDPAGPLPSPATTTRLRALGSHRLHPATETGG

REATSSPRPQPRDRRWGDTPPGRKPGSPVWGEGSYLSSYPTCPAQAWCSRS

ALRAPSSSLGAFFAGDLPPPLQAGAA
Bold—Signal domain
Italics—Transmembrane domain

The pre-T-alpha chain may lack a signal sequence as shown in SEQ ID NO: 30.

The native TM domain of the pre-T-alpha chain may be retained or replaced with that of a non-signalling polar anchor, the endodomain of CD3-Z and/or a co-stimulatory signal such as CD28 and/or 41BB. Suitable signalling endodomains and combinations thereof are described herein.

Illustrative B2M polypeptides linked to a TCR chain which are suitable for use in the present invention are shown as SEQ ID NO: 31 and 32. These polypeptide sequences comprise a B2M domain linked to the N-terminus of a pre-T-alpha chain and comprise a native pre-T-alpha transmembrane domain or a 41BB-CD3zeta signalling endodomain, respectively.

(B2M-L-PreTalpha)
SEQ ID NO: 31
MSRSVALAVLALLSLSGLEAIQRTPKIQVYSRHPAENGKSNFLNCYVSGFH

PSDIEVDLLKNGERIEKVEHSDLSFSKDWSFYLLYYTEFTPTEKDEYACRV

NHVTLSQPKIVKWDRDM*SGGGGSGGGGSGGGGS*TPFPSLAPPIMLLVDGKQ

QMVVVCLVLDVAPPGLDSPIWFSAGNGSALDAFTYGPSPATDGTWTNLAHL

SLPSEELASWEPLVCHTGPGAEGHSRSTQPMHLSGEASTARTCPQEPLRGI

PGGALWLGVLRLLLFKLLLFDLLLTCSCLCDPAGPLPSPATTTRLRALGSH

RLEPATETGGREATSSPRPQPRDRRWGDTPPGRKPGSPVWGEGSYLSSYPT

CPAQAWCSRSALRAPSSSLGAFFAGDLPPPLQAGAA
Bold—B2M domain
Italics—Linker domain
Standard —PreTalpha (B2M-L-PreTalpha-41BB-Z)
SEQ ID NO: 32
MSRSVALAVLALLSLSGLEAIQRTPKIQVYSRHPAENGKSNFLNCYVSGFH

PSDIEVDLLKNGERIEKVEHSDLSFSKDWSFYLLYYTEFTPTEKDEYACRV

NHVTLSQPKIVKWDRDM*SGGGGSGGGGSGGGGS*TPFPSLAPPIMLLVDGKQ

QMVVVCLVLDVAPPGLDSPIWFSAGNGSALDAFTYGPSPATDGTWTNLAHL

SLPSEELASWEPLVCHTGPGAEGHSRSTQPMHLSGEASTARTCPQEPLRGT

PGGIISFFLALISTALLFLLFFLTLRFSVVKRGRKKLLYIFKQPFMRPVQT

TQEEDGCSCRFPEEEERVKFSRSADAPAYQQGQNQLYNELNLGRREEYDVL

DKRRGRDPEMGGKPQRRKNPQEGLYNELQKDKMAEAYSEIGMKGERRRGKG

HDGLYQGLSTATKDTYDALHMQALPPR
Bold—B2M domain
Italics—Linker domain
Standard—PreTalpha
Underline—41BB-CD3z endodomain A B2M polypeptide linked to a component of the TCR complex and suitable for use in the present invention may comprise the sequence shown as SEQ ID NO: 31 or 32, or a variant thereof having at least 80% sequence identity. The variant having at least 80% sequence identity maintains ability to assemble with a MHC class I protein and facilitate productive peptide presentation by the MHC class I complex. It also enables an activating signal to be transmitted following binding of a TCR to the peptide/MHC complex comprising the engineered B2M.

The variant sequence of SEQ ID NO: 31 or SEQ ID NO: 32 may have at least 80, 85, 90, 95, 98 or 99% sequence identity, provided that the variant sequence retains the capacity to assemble with a MHC class I protein, facilitate productive peptide presentation by the MHC class I complex and transmit an activating signal following binding of a TCR to the peptide/MHC complex comprising the engineered B2M.

Suitably, the B2M polypeptide is linked to a component of the CD3 complex. The component of the CD3 complex to which a B2M polypeptide is linked may be selected from CD3-zeta, CD3-epsilon, CD3-gamma and CD3-delta.

Suitably the component of the CD3 complex to which a B2M polypeptide is linked is CD3-zeta.

Suitably the component of the CD3 complex to which a B2M polypeptide is linked is CD3-epsilon.

Suitably the component of the CD3 complex to which a B2M polypeptide is linked is CD3-gamma.

Suitably the component of the CD3 complex to which a B2M polypeptide is linked is CD3-delta.

Examples of human CD3ζ, CD3γ, CD3δ and CD3ε amino acid sequences are shown as SEQ ID NO: 4-7, respectively. The CD3 polypeptide sequence for use in the present invention may comprise the sequence shown as one of SEQ ID NO: 4-7 or a variant thereof having at least 80% sequence identity. For example, the variant may have at least 80, 85, 90, 95, 98 or 99% sequence identity to one of SEQ ID NO: 4-7.

(CD3ζ-amino acids 1-21 provide a signal peptide
which may be excluded)
SEQ ID NO: 4
MKWKALFTAAILQAQLPITEAQSFGLLDPKLCYLLDGILFIYGVILTALFL

RVKFSRSADAPAYQQGQNQLYNELNLGRREEYDVLDKRRGRDPEMGGKPQR

RKNPQEGLYNELQKDKMAEAYSEIGMKGERRRGKGHDGLYQGLSTAIKDTY

DALHMQALPPR (CD3γ-amino acids 1-22 provide a signal peptide
which may be excluded)
SEQ ID NO: 5
MEQGKGLAVLILAIILLQGTLAQSIKGNELVKVYDYQEDGSVLLTCDAEAK

NITWFKDGKMIGFLTEDKKKWNLGSNAKDPRGMYQCKGSQNKSKPLQVYYR

MCQNCIELNAATISGFLFAEIVSIFVLAVGVYFIAGQDGVRQSRASDKQTL

LPNDQLYQPLKDREDDQYSHLQGNQLRRN (CD3δ-amino acids 1-21 provide a signal peptide
which may be excluded)
SEQ ID NO: 6
MEHSTFLSGLVLATLLSQVSPFKIPIEELEDRVFVNCNTSITWVEGTVGTL

LSDITRLDLGKRILDPRGIYRCNGTDIYKDKESTVQVHYRMCQSCVELDPA

TVAGIIVTDVIATLLLALGVFCFAGHETGRLSGAADTQALLRNDQVYQPLR

DRDDAQYSHLGGNWARNK (CD3ε-amino acids 1-22 provide a signal peptide
which may be excluded)
SEQ ID NO: 7
MQSGTHWRVLGLCLLSVGVWGQDGNEEMGGITQTPYKVSISGTTVILTCPQ

YPGSEILWQHNDKNIGGDEDDKNIGSDEDHLSLKEFSELEQSGYYVCYPRG

SKPEDANFYLYLRARVCENCMEMDVMSVATIVIVDICITGGLLLLVYYWSK

NRKAKAKPVTRGAGAGGRQRGQNKERPPPVPNPDYEPIRKGQRDLYSGLNQ

RRI

The B2M polypeptide may be linked to the CD3 component by any suitable means. For example, the B2M polypeptide may be fused to the component of the CD3 complex by a linker peptide.

Suitable linker peptides are known in the art. For example, a range of suitable linker peptides are described by Chen et al. (Adv Drug Deliv Rev. 2013 Oct. 15; 65(10): 1357-1369—see Table 3 in particular).

A suitable linker is an (SGGGG)n (SEQ ID NO: 29), which comprises one or more copies of SEQ ID NO: 29. For example, a suitable linker peptide is shown as SEQ ID NO: 8.

SEQ ID NO: 8
SGGGGSGGGGSGGGGS

Suitably, the B2M polypeptide is linked to the ectodomain of the component of the CD3 complex. Suitably, the B2M polypeptide is linked to the N-terminus of the component of the CD3 complex.

Illustrative B2M polypeptides linked to a component of the CD3 complex which are suitable for use in the present invention are shown as SEQ ID NO: 9 and 10. These polypeptide sequences comprise a B2M domain linked to the N-terminus of a CD3ε polypeptide or a CD3ζ polypeptide, respectively.

(B2M-CD3ε)
SEQ ID NO: 9
MSRSVALAVLALLSLSGLEAIQRTPKIQVYSRHPAENGKSNFLNCYVSGFH

PSDIEVDLLKNGERIEKVEHSDLSFSKDWSFYLLYYTEFTPTEKDEYACRV

NHVTLSQPKIVKWDRDM*SGGGGSGGGGSGGGGS*QDGNEEMGGITQTPYKVS

ISGTTVILTCPQYPGSEILWQHNDKNIGGDEDDKNIGSDEDHLSLKEFSEL

EQSGYYVCYPRGSKPEDANFYLYLRARVCENCMEMDVMSVATIVIVDICIT

GGLLLLVYYWSKNRKAKAKPVTRGAGAGGRQRGQNKERPPPVPNPDYEPIR

KGQRDLYSGLNQRRI

-continued

Bold—B2M domain
Italics—Linker domain
Standard—CD3E (B2M-CD3ζ)

SEQ ID NO: 10

MSRSVALAVLALLSLSGLEAIQRTPKIQVYSRHPAENGKSNFLNCYVSGFH

PSDIEVDLLKNGERIEKVEHSDLSFSKDWSFYLLYYTEFTPTEKDEYACRV

NHVTLSQPKIVKWDRDM*SGGGGSGGGGSGGGGS*QSFGLLDPKLCYLLDGIL

FIYGVILTALELRVKFSRSADAPAYQQGQNQLYNELNLGRREEYDVLDKRR

GRDPEMGGKPQRRKNPQEGLYNELQKDKMAEAYSEIGMKGERRRGKGHDGL

YQGLSTATKDTYDALHMQALPPR

Bold—B2M domain
Italics—Linker domain
Standard—CD3E

A B2M polypeptide linked to a component of the CD3 complex and suitable for use in the present invention may comprise the sequence shown as SEQ ID NO: 9 or 10, or a variant thereof having at least 80% sequence identity. The variant having at least 80% sequence identity maintains ability to assemble with a MHC class I protein and facilitate productive peptide presentation by the MHC class I complex. It also enables an activating signal to be transmitted following binding of a TCR to the peptide/MHC complex comprising the engineered B2M.

The variant sequence of SEQ ID NO: 9 or SEQ ID NO: 10 may have at least 80, 85, 90, 95, 98 or 99% sequence identity, provided that the variant sequence retains the capacity to assemble with a MHC class I protein, facilitate productive peptide presentation by the MHC class I complex and transmit an activating signal following binding of a TCR to the peptide/MHC complex comprising the engineered B2M.

In a further independent aspect, the present invention provides an engineered B2M polypeptide that is linked to a component of the CD3 complex as described herein.

The present invention further provides a polynucleotide encoding an engineered B2M polypeptide linked to a component of the CD3 complex as described herein. The invention also provides a vector comprising said polynucleotide.

Further, the present invention provides a cell which comprises an engineered B2M polypeptide linked to a component of the CD3 complex or a polynucleotide or a vector which encodes said engineered B2M polypeptide.

Bispecific B2M/TCR Binding Molecule

In further embodiments of the present invention, the polypeptide capable of co-localizing the B2M component of the MHC class I molecule with an intracellular signalling domain may be a bispecific polypeptide which comprises; (i) a first binding domain which is capable of binding to the B2M polypeptide and (ii) a second binding domain which is capable of binding to a polypeptide comprising an intracellular signalling domain or a component of the CD3 complex.

When expressed on the cell surface, the present bispecific molecule co-localises MHC class I and the TCR, and facilitates TCR signalling in a cell of the present invention following binding of a TCR on a different T cell to the peptide/MHC complex bound by the present bispecific molecule.

Bispecific molecules have been developed in a number of different formats. One of the most common is a fusion consisting of two single-chain variable fragments (scFvs) of different antibodies.

The first and/or second binding domains of the present bispecific molecule may be antibody or immunoglobulin based binding domains.

As used herein, "antibody" means a polypeptide having an antigen binding site which comprises at least one complementarity determining region CDR. The antibody may comprise 3 CDRs and have an antigen binding site which is equivalent to that of a domain antibody (dAb). The antibody may comprise 6 CDRs and have an antigen binding site which is equivalent to that of a classical antibody molecule. The remainder of the polypeptide may be any sequence which provides a suitable scaffold for the antigen binding site and displays it in an appropriate manner for it to bind the antigen. The antibody may be a whole immunoglobulin molecule or a part thereof such as a Fab, F(ab)'$_2$, Fv, single chain Fv (ScFv) fragment, Nanobody or single chain variable domain (which may be a VH or VL chain, having 3 CDRs). The antibody may be a bifunctional antibody. The antibody may be non-human, chimeric, humanised or fully human.

Alternatively, the first and/or second binding domains of the present bispecific molecule may comprise domains which are not derived from or based on an immunoglobulin. A number of "antibody mimetic" designed repeat proteins (DRPs) have been developed to exploit the binding abilities of non-antibody polypeptides. Such molecules include ankyrin or leucine-rich repeat proteins e.g. DARPins (Designed Ankyrin Repeat Proteins), Anticalins, Avimers and Versabodies.

The first binding domain of the present bispecific molecule is capable of binding to a B2M polypeptide.

In particular, the first binding domain may be capable of binding to B2Mb. Suitable B2Mb binding domains are known in the art and include, for example, the polypeptide sequence shown as SEQ ID NO: 11.

SEQ ID NO: 11

EVQLQQSGAELVKPGASVKLSCIPSGFNVKDTYIHWVKQRPKQGLEWIGRI

DPSDGDIKYDPKFQGKATITADTSSNTVSLQLSSLTSEDTAVYYCARWFGD

YGAMNYWGQGTSVTVSSGGGGSGGGGSGGGGSDILMTQSPASQSASLGESV

TITCLASQTIGTWLAWYQQKPGKSPQLLIYAATSLADGVPSRFSGSGSGTK

FSLKIRTLQAEDFVSYYCQQLYSKPYTFGGGTKLEIKR

This B2Mb binding domain may be generated from the BBM1 hybridoma described by Brodsky et al. (Eur. J. Immunol; 9; 536-545; 1979) and Parham et al. (J. Biol. Chem.; 258; 6179-6186; 1983).

The first binding domain may comprise the complementarity determining regions (CDRs) from the scFv sequence shown as SEQ ID NO: 11.

The first domain may comprise a scFv sequence, such as the one shown as SEQ ID NO: 11. The second domain may comprise a variant of such a sequence which has at least 80% sequence identity to SEQ ID NO: 11 and binds B2M, in particular B2Mb.

The first binding domain may comprise one or more CDRs from the sequence shown as SEQ ID NO: 11. The second binding domain may comprise CDR3 from the heavy-chain of SEQ ID NO: 11 and/or CDR3 from the light chain of SEQ ID NO: 11. The second binding domain may comprise all 6 CDRs from SEQ ID NO: 11. The sequences of the CDRs from SEQ ID NO: 11 are shown below.

```
Heavy Chain
CDR1:
                                           (SEQ ID NO: 33)
GFNVKDT

CDR2:
                                           (SEQ ID NO: 34)
DPSDGD

CDR3:
                                           (SEQ ID NO: 35)
WFGDYGAMNY

Light Chain
CDR1:
                                           (SEQ ID NO: 36)
LASQTIGTWLA

CDR2:
                                           (SEQ ID NO: 37)
AATSLAD

CDR3:
                                           (SEQ ID NO: 38)
QQLYSKPYT
```

The first binding domain may comprise a scFv which comprises the CDR sequences from SEQ ID NO: 11 (as shown in SEQ ID NO: 33-38).

By way of example only, a further hybridoma providing antibodies against B2M are described by Mhashilkar et al. (Gene Ther.; 995); 207-319; 2002). The BB7.7 hybridoma described by Mhashilkar et al. was found to express on variable heavy chain sequence and two possible variable light chain sequences. The first binding domain may comprise an scFV generated from the BB7.7 (shown as SEQ ID NO: 39-40).

```
                                           SEQ ID NO: 39
QVQLQQSGAELARPGASVKLSCKASGYTFTSHWMQWVRQRPGQGLEWICTI

YPGDGDTRYTQNFKGKATLTADKSSTTAYLHLSSLSSEDSAVYYCARDEIT

TVVPRGFAYWGQGTSVTVSSGGGGSGGGGSGGGGSELVLTQTPSSLSASLG

DRVTISCRASQDISSYLNWYQQKPDGTIKLLIYYTSRLYSCVPPRFSGSGA

GTDYSLTISNLEQEDIATYFCQQGNVIPYTFCGGTKLEMKR

SEQ ID NO: 40
QVQLQQSGAELTRPGASVKLSCKASGYTFTSHWMQWVRQRPGQGLEWIGTI

YPGDGDTRYTQNFKGKATLTADKSSTTAYLHLSSLSSEDSAVYYCARDEIT

TVVPRGFAYWGQGTLVTVSSGGGGSGGGGSGGGGSELVLTQSPSSLSASLG

DTITITCHASQNINVWLSWYQQKPGNIPQLLIYKASNLHTGVPSRFSGRGS

GTGFTLTISSLQPEDIGTYYCQQGQSYPLTFGGGTKLEMKR
```

The first binding domain may comprise the scFv sequence shown as SEQ ID NO: 11, 39 or 40 or a variant thereof having at least 80% sequence identity, which retains the capacity to bind B2M.

A variant sequence from SEQ ID NO: 11, 39 or 40 may have at least 80, 85, 90, 95, 98 or 99% sequence identity and have equivalent or improved B2M binding capabilities as a sequence shown as SEQ ID NO: 11, 39 or 40.

The second domain of the present bispecific molecule is capable of binding to a polypeptide comprising an intracellular signalling domain or a component of the CD3 complex. In particular, the second domain may be capable of binding CD3 on the T-cell surface. In this respect, the second domain may comprise a CD3 or TCR-specific antibody or part thereof.

The second domain may comprise the complementarity determining regions (CDRs) from the scFv sequence shown as SEQ ID NO: 12.

The second domain may comprise a scFv sequence, such as the one shown as SEQ ID NO: 12. The second domain may comprise a variant of such a sequence which has at least 80% sequence identity and binds CD3.

The second domain may comprise an antibody or part thereof which specifically binds CD3, such as OKT3, WT32, anti-leu-4, UCHT-1, SPV-3TA, TR66, SPV-T3B or affinity tuned variants thereof.

The second domain of the bispecific molecule of the invention may comprise all or part of the monoclonal antibody OKT3, which was the first monoclonal antibody approved by the FDA. OKT3 is available from ATCC CRL 8001. The antibody sequences are published in U.S. Pat. No. 7,381,803.

The second domain may comprise one or more CDRs from OKT3. The second binding domain may comprise CDR3 from the heavy-chain of OKT3 and/or CDR3 from the light chain of OKT3. The second binding domain may comprise all 6 CDRs from OKT3, as shown below.

```
Heavy Chain
CDR1:
                                           (SEQ ID NO: 13)
KASGYTFTRYTMH CDR2:
                                           (SEQ ID NO: 14)
INPSRGYTNYNQKFKD

CDR3:
                                           (SEQ ID NO: 15)
YYDDHYCLDY

Light Chain
CDR1:
                                           (SEQ ID NO: 16)
SASSSVSYMN

CDR2:
                                           (SEQ ID NO: 17)
RWIYDTSKLAS

CDR3:
                                           (SEQ ID NO: 18)
QQWSSNPFT
```

The second binding domain may comprise a scFv which comprises the CDR sequences from OKT3. The second binding domain may comprise the scFv sequence shown below as SEQ ID NO: 12 or 41 or a variant thereof having at least 80% sequence identity, which retains the capacity to bind CD3.

```
                                           SEQ ID NO: 12
QVQLQQSGAELARPGASVKMSCKASGYTFTRYTMEWVKQRPGQGLEWIGYI

NPSRGYTNYNQKFKDKATLITDKSSSTAYMQLSSLISEDSAVYYCARYYDD

HYCLDYWGQGTTLIVSSSGGGGSGGGGSGGGGSQIVLTQSPAIMSASPGEK

VTMTCSASSSVSYMNWYQQKSGTSPKRWIYDTSKLASGVPAHFRGSGSGTS

YSLTISGMEAEDAATYYCQQWSSNPFTFGSGTKLEINR

SEQ ID NO: 41
QIVLTQSPAIMSASPGEKVIMICSASSSVSYMNWYQQKSGTSPKRWIYDTS

KLASGVPAHFRGSGSGTSYSLTISGMEAEDAATYYCQQWSSNPFTFGSGTK
```

```
-continued
LEINRSSSGGGGSGGGGSGGGGSQVQLQQSGAELARPGASVKMSCKASGYT

FTRYTMHWVKQRPGQGLEWIGYINPSRGYTNYNQKFKDKATLTIDKSSSTA

YMQLSSLTSEDSAVYYCARYYDDHYCLDYWGQGTTLTVSS
```

SEQ ID NO: 12 and 41 provide alternative architectures of an scFV suitable for use in the present invention. SEQ ID NO: 12 is provided as a VL-VH arrangement. SEQ ID NO: 41 is provided as a VH-VL arrangement.

A variant sequence from SEQ ID NO: 12 or 41 may have at least 80, 85, 90, 95, 98 or 99% sequence identity and have equivalent or improved CD3 binding capabilities as the sequence shown as SEQ ID NO: 12 or 41.

The bispecific molecule of the present invention may comprise a spacer sequence to connect the first domain with the second domain and spatially separate the two domains.

For example, the first and second binding domains may be connected via a short five residue peptide linker (GGGGS).

The spacer sequence may, for example, comprise an IgG1 hinge or a CD8 stalk. The linker may alternatively comprise an alternative linker sequence which has similar length and/or domain spacing properties as an IgG1 hinge or a CD8 stalk.

The spacer may be a short spacer, for example a spacer which comprises less than 100, less than 80, less than 60 or less than 45 amino acids. The spacer may be or comprise an IgG1 hinge or a CD8 stalk or a modified version thereof.

Examples of amino acid sequences for these linkers are given below:

```
(IgG1 hinge):
                                           SEQ ID NO: 19
AEPKSPDKTHTCPPCPKDPKSGGGGS (CD8 stalk):
                                           SEQ ID NO: 20
TTTPAPRPPTPAPTIASQPLSLRPEACRPAAGGAVHTRGLDFACD
```

The CD8 stalk has a sequence such that it may induce the formation of homodimers. If this is not desired, one or more cysteine residues may be substituted or removed from the CD8 stalk sequence. The bispecific molecule of the invention may include a spacer which comprises or consists of the sequence shown as SEQ ID NO: 20 or a variant thereof having at least 80, 85, 90, 95, 98 or 99% sequence identity, provided that the variant sequence is a molecule which causes approximately equivalent spacing of the first and second domains and/or that the variant sequence causes homodimerisation of the bispecific molecule.

The bispecific molecule of the invention may have the general formula:

First domain–spacer–second domain.

The spacer may also comprise one or more linker motifs to introduce a chain-break. A chain break separate two distinct domains but allows orientation in different angles. Such sequences include the sequence SDP, and the sequence SGGGSDP (SEQ ID NO: 21).

The linker may comprise a serine-glycine linker, such as SGGGGS (SEQ ID NO: 22).

The spacer may cause the bispecific molecule to form a homodimer, for example due to the presence of one or more cysteine residues in the spacer, which can form a di-sulphide bond with another molecule comprising the same spacer.

The bispecific molecule may be membrane-tethered. In other words, the bispecific molecule may comprise a transmembrane domain such that it is localised to the cell membrane following expression in the cell of the present invention.

By way of example, the transmembrane domain may a transmembrane domain as described herein. For example, the transmembrane domain may comprise a hydrophobic alpha helix. The transmembrane domain may be derived from CD8alpha or CD28.

By way of example, the transmembrane domains of CD8alpha and CD28 are shown herein as SEQ ID NO: 28 and SEQ ID NO: 2, respectively.

The bispecific molecule of the invention may have the general formula:

First domain–spacer–second domain—transmembrane domain; or

Transmembrane domain–first domain–spacer–second domain.

An illustrative bispecific molecule suitable for use in the present invention is shown as SEQ ID NO: 23. This polypeptide sequences comprises a B2M-binding domain linked to a CD3-binding and a transmembrane domain.

```
(aB2M-L-aCD3-TM-A)
                                           SEQ ID NO: 23
METDTLLLWVLLLWVPGSTGEVQLQQSGAELVKPGASVKLSCTPSGFNVKD

TYIHWVKQRPKQGLEWIGRIDPSDGDIKYDPKFQGKATITADTSSNTVSLQ

LSSLTSEDTAVYYCARWFGDYGAMNYWGQGTSVTVSSGGGGSGGGGSGGGG

SDILMTQSPASQSASLGESVTITCLASQTIGTWLAWYQQKPGKSPQLLIYA

ATSLADCVPSRFSGSGSGTKFSLKIRTLQAEDFVSYYCQQLYSKPYTEGGG

TKLEIKRSGGGGSGGGGSGGGGSQIVLTQSPAIMSASPGEKVTMTCSASSS

VSYMNWYQQKSGTSPKRWIYDTSKLASGVPAHFRGSGSGTSYSLTISGMEA

EDAATYYCQQWSSNPFTFGSGTKLEINRSSSGGGGSGGGGSGGGGS

QVQLQQSGAELARPGASVKMSCKASGYTFTRYTMHWVKQRP

GQGLEWIGYINPSRGYTNYNQKFKDKATLTTDKSSSTAYMQLSSLT

SEDSAVYYCARYYDDHYCLDYWGQGTTLTVSSSGGGGSGGGGSGGGGSIY

IWAPLATCGVLLLSLVITLYCNHRNRRRVCKCPRP
Bold—Signal
Normal—aB2M-VH
Italics—Linker
Underline—aB2M-VL
Bold/Underline—aCD3-VL
Bold/Italics/Underline—aCD3-VH
Underline—Transmembrane and anchor
```

A bispecific molecule suitable for use in the present invention may comprise the sequence shown as SEQ ID NO: 23, or a variant thereof having at least 80% sequence identity. The variant having at least 80% sequence identity maintains ability to bind B2M and an intracellular signalling domain or a component of the CD3 complex. The present bispecific molecule also enables an activating signal to be transmitted following binding of a TCR to the peptide/MHC complex comprising the B2M which is bound by the bispecific molecule.

The variant sequence of SEQ ID NO: 23 may have at least 80, 85, 90, 95, 98 or 99% sequence identity, provided that the variant sequence retains the capacity to bind B2M and an intracellular signalling domain or a component of the CD3 complex; and enable an activating signal to be transmitted following binding of a TCR to the peptide/MHC complex comprising the B2M which is bound by the bispecific molecule.

In a further independent aspect, the present invention provides a bispecific molecule comprising: (i) a first binding domain which is capable of binding to the B2M polypeptide and (ii) a second binding domain which is capable of binding to a polypeptide comprising an intracellular signalling domain or a component of the CD3 complex as described herein.

The present invention further provides a polynucleotide encoding bispecific molecule comprising: (i) a first binding domain which is capable of binding to the B2M polypeptide and (ii) a second binding domain which is capable of binding to a polypeptide comprising an intracellular signalling domain or a component of the CD3 complex as described herein. The invention also provides a vector comprising said polynucleotide.

Further, the present invention provides a cell which comprises a bispecific molecule as described herein; or a polynucleotide or a vector which encodes said engineered B2M polypeptide.

Intracellular Signalling Domain

The present invention involves providing a polypeptide capable of co-localizing a beta-2 microglobulin component of a MHC class I molecule with an intracellular signalling domain within the cell.

An intracellular signalling domain as used herein refers to a signal-transmission portion of an endomain.

The intracellular signalling domain is capable of leading to signalling within the cell of the present invention following binding of a TCR present on a reactive T cell to the MHC/peptide complex comprising the engineered B2M in the cell of the present invention.

The intracellular signalling domain may be or comprise a T cell signalling domain.

The intracellular signalling domain may comprise one or more immunoreceptor tyrosine-based activation motifs (ITAMs). An ITAM is a conserved sequence of four amino acids that is repeated twice in the cytoplasmic tails of certain cell surface proteins of the immune system. The motif contains a tyrosine separated from a leucine or isoleucine by any two other amino acids, giving the signature YxxL/I. Two of these signatures are typically separated by between 6 and 8 amino acids in the tail of the molecule (YxxL/Ix$_{(6-8)}$YxxL/I).

ITAMs are important for signal transduction in immune cells. Hence, they are found in the tails of important cell signalling molecules such as the CD3 and ζ-chains of the T cell receptor complex, the CD79 alpha and beta chains of the B cell receptor complex, and certain Fc receptors. The tyrosine residues within these motifs become phosphorylated following interaction of the receptor molecules with their ligands and form docking sites for other proteins involved in the signalling pathways of the cell.

Preferably, the intracellular signalling domain component comprises, consists essentially of, or consists of the CD3-ζ endodomain, which contains three ITAMs. Classically, the CD3-ζ endodomain transmits an activation signal to the T cell after antigen is bound. However, in the context of the present invention, the CD3-ζ endodomain transmits an activation signal to the T cell after the MHC/peptide complex comprising the engineered B2M binds to a TCR on a different T cell.

The intracellular signalling domain may comprise additional co-stimulatory signalling. For example, 4-1BB (also known as CD137) can be used with CD3-ζ, or CD28 and OX40 can be used with CD3-ζ to transmit a proliferative/survival signal.

Accordingly, intracellular signalling domain may comprise the CD3-ζ endodomain alone, the CD3-ζ endodomain in combination with one or more co-stimulatory domains selected from 4-1BB, CD28 or OX40 endodomain, and/or a combination of some or all of 4-1BB, CD28 or OX40.

The endodomain may comprise one or more of the following: an ICOS endodomain, a CD2 endodomain, a CD27 endodomain, or a CD40 endodomain.

The endomain may comprise the sequence shown as SEQ ID NO: 24 to 27 or a variant thereof having at least 80% sequence identity. The variant having at least sequence identity maintains the signalling function of one of SEQ ID NO: 24 to 27.

The variant of one of the sequence shown as SEQ ID NO: 24 to 27 may have at least 80, 85, 90, 95, 98 or 99% sequence identity, provided that the variant sequence retains the capacity to transmit an activating signal to the cell.

The percentage identity between two polypeptide sequences may be readily determined by programs such as BLAST, which is freely available at http://blast.ncbi.nlm.nih.gov. Suitably, the percentage identity is determined across the entirety of the reference and/or the query sequence.

```
CD3-ζ endodomain
                                        SEQ ID NO: 24
RVKFSRSADAPAYQQGQNQLYNELNLGRREEYDVLDKRRGRDPEMGGKPRR

KNPQEGLYNELQKDKMAEAYSEIGMKGERRRGKGHDGLYQGLSTATKDTYD

ALHMQALPPR 4-1BB and CD3-ζ endodomains
                                        SEQ ID NO: 25
MGNSCYNIVATLLLVLNFERTRSLQDPCSNCPAGTFCDNNRNQICSPCPPN

SFSSAGGQRTCDICRQCKGVFRTRKECSSTSNAECDCTPGFHCLGAGCSMC

EQDCKQGQELTKKGCKDCCFGTFNDQKRGICRPWTNCSLDGKSVLVNGTKE

RDVVCGPSPADLSPGASSVTPPAPAREPGHSPQIISFFLALTSTALLFLLF

FLTLRFSVVKRGRKKLLYIFKQPFMRPVQTTQEEDGCSCRFPEEEEGGCEL

RVKFSRSADAPAYQQGQNQLYNELNLGRREEYDVLDKRRGRDPEMGGKPQR

RKNPQEGLYNELQKDKMAEAYSEIGMKGERRRGKGHDGLYQGLSTATKDTY

DALHMQALPPR

CD28 and CD3-ζ endodomains
                                        SEQ ID NO: 26
SKRSRLLHSDYMNMTPRRPGPTRKHYQPYAPPRDFAAYRSRVKFSRSADAP

AYQQGQNQLYNELNLGRREEYDVLDKRRGRDPEMGGKPRRKNPQEGLYNEL

QKDKMAEAYSEIGMKGERRRGKGHDGLYQGLSTATKDTYDALHMQALPPR

CD28, OX40 and CD3-ζ endodomains
                                        SEQ ID NO: 27
SKRSRLLHSDYMNMTPRRPGPTRKHYQPYAPPRDFAAYRSRDQRLPPDAHK

PPGGGSFRTPIQEEQADAHSTLAKIRVKFSRSADAPAYQQGQNQLYNELNL

GRREEYDVLDKRRGRDPEMGGKPRRKNPQEGLYNELQKDKMAEAYSEIGMK

GERRRGKGHDGLYQGLSTATKDTYDALHMQALPPR
```

Signal Peptide

The present polypeptide capable of co-localizing a B2M component of a MHC class I molecule with an intracellular signalling domain within the cell may comprise a signal peptide so that when it is expressed in a cell, such as a T-cell, the nascent protein is directed to the endoplasmic reticulum and subsequently to the cell surface, where it is expressed.

The core of the signal peptide may contain a long stretch of hydrophobic amino acids that has a tendency to form a single alpha-helix. The signal peptide may begin with a short positively charged stretch of amino acids, which helps to enforce proper topology of the polypeptide during translocation. At the end of the signal peptide there is typically a stretch of amino acids that is recognized and cleaved by signal peptidase. Signal peptidase may cleave either during or after completion of translocation to generate a free signal peptide and a mature protein. The free signal peptides are then digested by specific proteases.

Cell

The cell of the present invention may be an immune effector cell, such as a T-cell, a natural killer (NK) cell or a cytokine induced killer cell.

The T cell may be an alpha-beta T cell or a gamma-delta T cell.

The cell may be derived from a patient's own peripheral blood (1st party), or in the setting of a haematopoietic stem cell transplant from donor peripheral blood (2nd party), or peripheral blood from an unconnected donor (3rd party). T or NK cells, for example, may be activated and/or expanded prior to being transduced with nucleic acid molecule(s) encoding the polypeptides of the invention, for example by treatment with an anti-CD3 monoclonal antibody.

Alternatively, the cell may be derived from ex vivo differentiation of inducible progenitor cells or embryonic progenitor cells to T cells. Alternatively, an immortalized T-cell line which retains its lytic function may be used.

Figure 3:
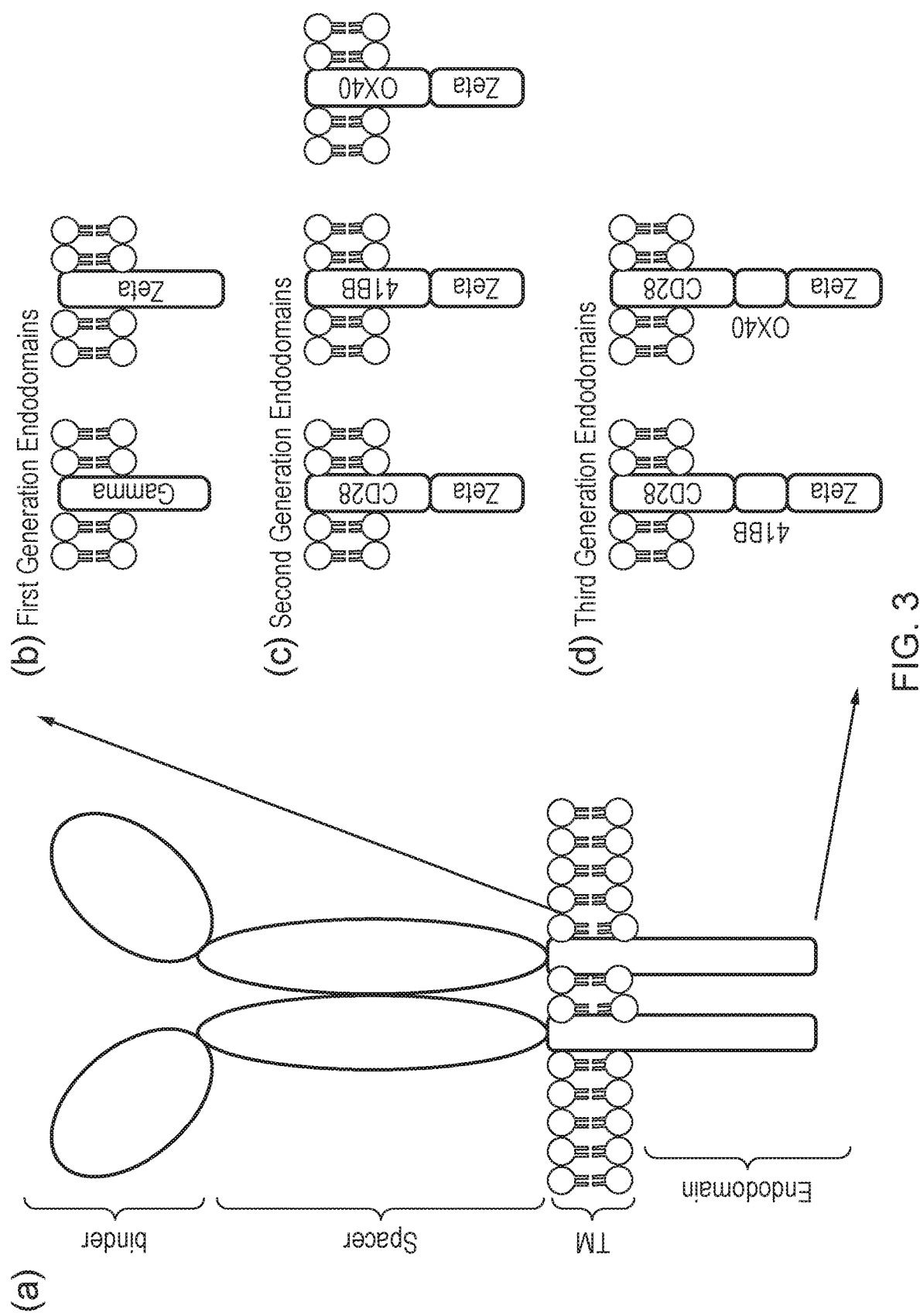
FIG. 3—a) Schematic diagram illustrating a classical CAR. (b) to (d): Different generations and permutations of CAR endodomains: (b) initial designs transmitted ITAM signals alone through FcεR1-γ or CD3ζ endodomain, while later designs transmitted additional (c) one or (d) two co-stimulatory signals in the same compound endodomain.

The cell may be a haematopoietic stem cell (HSC). HSCs can be obtained for transplant from the bone marrow of a suitably matched donor, by leukopheresis of peripheral blood after mobilization by administration of pharmacological doses of cytokines such as G-CSF [peripheral blood stem cells (PBSCs)], or from the umbilical cord blood (UCB) collected from the placenta after delivery. The marrow, PBSCs, or UCB may be transplanted without processing, or the HSCs may be enriched by immune selection with a monoclonal antibody to the CD34 surface antigen Chimeric Antigen Receptor Classical CARs, which are shown schematically in FIG. 3, are chimeric type I trans-membrane proteins which connect an extracellular antigen-recognizing domain (binder) to an intracellular signalling domain (endodomain). The binder is typically a single-chain variable fragment (scFv) derived from a monoclonal antibody (mAb), but it can be based on other formats which comprise an antibody-like antigen binding site or on a ligand for the target antigen. A spacer domain may be necessary to isolate the binder from the membrane and to allow it a suitable orientation. A common spacer domain used is the Fc of IgG1. More compact spacers can suffice e.g. the stalk from CD8α and even just the IgG1 hinge alone, depending on the antigen. A trans-membrane domain anchors the protein in the cell membrane and connects the spacer to the endodomain.

Early CAR designs had endodomains derived from the intracellular parts of either the γ chain of the FcεR1 or CD3ζ. Consequently, these first generation receptors transmitted immunological signal 1, which was sufficient to trigger T-cell killing of cognate target cells but failed to fully activate the T-cell to proliferate and survive. To overcome this limitation, compound endodomains have been constructed: fusion of the intracellular part of a T-cell co-stimulatory molecule to that of CD3ζ results in second generation receptors which can transmit an activating and co-stimulatory signal simultaneously after antigen recognition. The co-stimulatory domain most commonly used is that of CD28. This supplies the most potent co-stimulatory signal—namely immunological signal 2, which triggers T-cell proliferation. Some receptors have also been described which include TNF receptor family endodomains, such as the closely related OX40 and 41BB which transmit survival signals. Even more potent third generation CARs have now been described which have endodomains capable of transmitting activation, proliferation and survival signals.

CAR-encoding nucleic acids may be transferred to T cells using, for example, retroviral vectors. In this way, a large number of antigen-specific T cells can be generated for adoptive cell transfer. When the CAR binds the target-antigen, this results in the transmission of an activating signal to the T-cell it is expressed on. Thus the CAR directs the specificity and cytotoxicity of the T cell towards cells expressing the targeted antigen.

Antigen Binding Domain

The antigen-binding domain is the portion of a classical CAR which recognizes antigen.

Numerous antigen-binding domains are known in the art, including those based on the antigen binding site of an antibody, antibody mimetics, and T-cell receptors. For example, the antigen-binding domain may comprise: a single-chain variable fragment (scFv) derived from a monoclonal antibody; a natural ligand of the target antigen; a peptide with sufficient affinity for the target; a single domain binder such as a camelid; an artificial binder single as a Darpin; or a single-chain derived from a T-cell receptor.

Various tumour associated antigens (TAA) are known, as shown in the following Table 2. The antigen-binding domain used in the present invention may be a domain which is capable of binding a TAA as indicated therein.

TABLE 1

| Cancer type | TAA |
| --- | --- |
| Diffuse Large B-cell Lymphoma | CD19, CD20 |
| Breast cancer | ErbB2, MUC1 |
| AML | CD13, CD33 |
| Neuroblastoma | GD2, NCAM, ALK, GD2 |
| B-CLL | CD19, CD52, CD160 |
| Colorectal cancer | Folate binding protein, CA-125 |
| Chronic Lymphocytic Leukaemia | CD5, CD19 |
| Glioma | EGFR, Vimentin |
| Multiple myeloma | BCMA, CD138 |
| Renal Cell Carcinoma | Carbonic anhydrase IX, G250 |
| Prostate cancer | PSMA |
| Bowel cancer | A33 |

The antigen-binding domain may comprise a proliferation-inducing ligand (APRIL) which binds to B-cell membrane antigen (BCMA) and transmembrane activator and calcium modulator and cyclophilin ligand interactor (TACI). A CAR comprising an APRIL-based antigen-binding domain is described in WO2015/052538.

Transmembrane Domain

The transmembrane domain is the sequence of a classical CAR that spans the membrane. It may comprise a hydrophobic alpha helix. The transmembrane domain may be derived from CD28, which gives good receptor stability.

Signal Peptide

The CAR may further comprise a signal peptide as described herein.

Spacer Domain

The CAR may comprise a spacer sequence to connect the antigen-binding domain with the transmembrane domain. A flexible spacer allows the antigen-binding domain to orient in different directions to facilitate binding.

The spacer sequence may, for example, comprise an IgG1 Fc region, an IgG1 hinge or a human CD8 stalk or the mouse CD8 stalk. The spacer may alternatively comprise an alternative linker sequence which has similar length and/or domain spacing properties as an IgG1 Fc region, an IgG1 hinge or a CD8 stalk. A human IgG1 spacer may be altered to remove Fc binding motifs.

Intracellular Signalling Domain

The intracellular signalling domain is the signal-transmission portion of a classical CAR.

The most commonly used signalling domain component is that of CD3-zeta endodomain, which contains 3 ITAMs. This transmits an activation signal to the T cell after antigen is bound. CD3-zeta may not provide a fully competent activation signal and additional co-stimulatory signalling may be needed. For example, chimeric CD28 and OX40 can be used with CD3-Zeta to transmit a proliferative/survival signal, or all three can be used together (illustrated in FIG. 3B).

Transgenic T-Cell Receptor

The T-cell receptor (TCR) is a molecule found on the surface of T cells which is responsible for recognizing fragments of antigen as peptides bound to major histocompatibility complex (MHC) molecules.

The TCR is a heterodimer composed of two different protein chains. In humans, in 95% of T cells the TCR consists of an alpha (α) chain and a beta (β) chain (encoded by TRA and TRB, respectively), whereas in 5% of T cells the TCR consists of gamma and delta (γ/δ) chains (encoded by TRG and TRD, respectively).

When the TCR engages with antigenic peptide and MHC (peptide/MHC), the T lymphocyte is activated through signal transduction.

In contrast to conventional antibody-directed target antigens, antigens recognized by the TCR can include the entire array of potential intracellular proteins, which are processed and delivered to the cell surface as a peptide/MHC complex.

It is possible to engineer cells to express heterologous (i.e. non-native) TCR molecules by artificially introducing the TRA and TRB genes; or TRG and TRD genes into the cell using vector. For example the genes for engineered TCRs may be reintroduced into autologous T cells and transferred back into patients for T cell adoptive therapies. Such 'heterologous' TCRs may also be referred to herein as 'transgenic TCRs'.

Nucleic Acid Construct/Kit Of Nucleic Acid Sequences

The present invention provides a nucleic acid sequence which comprises: (i) a first nucleic acid sequence which encodes a chimeric antigen receptor (CAR) or a transgenic TCR; and (ii) a second nucleic acid sequence which encodes a polypeptide capable of co-localizing a beta-2 microglobulin component of a MHC class I molecule with an intracellular signalling domain as defined herein.

The present invention further provides a kit comprising nucleic acid sequences according to the present invention. For example, the kit may comprise (i) a first nucleic acid sequence which encodes a chimeric antigen receptor (CAR) or a transgenic TCR; and (ii) a second nucleic acid sequence which encodes a polypeptide capable of co-localizing a beta-2 microglobulin component of a MHC class I molecule with an intracellular signalling domain as defined herein.

As used herein, the terms "polynucleotide", "nucleotide", and "nucleic acid" are intended to be synonymous with each other.

It will be understood by a skilled person that numerous different polynucleotides and nucleic acids can encode the same polypeptide as a result of the degeneracy of the genetic code. In addition, it is to be understood that skilled persons may, using routine techniques, make nucleotide substitutions that do not affect the polypeptide sequence encoded by the polynucleotides described here to reflect the codon usage of any particular host organism in which the polypeptides are to be expressed.

Nucleic acids according to the invention may comprise DNA or RNA. They may be single-stranded or double-stranded. They may also be polynucleotides which include within them synthetic or modified nucleotides. A number of different types of modification to oligonucleotides are known in the art. These include methylphosphonate and phosphorothioate backbones, addition of acridine or polylysine chains at the 3' and/or 5' ends of the molecule. For the purposes of the use as described herein, it is to be understood that the polynucleotides may be modified by any method available in the art. Such modifications may be carried out in order to enhance the in vivo activity or life span of polynucleotides of interest.

The terms "variant", "homologue" or "derivative" in relation to a nucleotide sequence include any substitution of, variation of, modification of, replacement of, deletion of or addition of one (or more) nucleic acid from or to the sequence.

Co-Expression Site

A co-expression site is used herein to refer to a nucleic acid sequence enabling co-expression of both (i) a CAR or a TCR; and (ii) a polypeptide capable of co-localizing a beta-2 microglobulin component of a MHC class I molecule with an intracellular signalling domain within the cell. The co-expression site may be a sequence encoding a cleavage site, such that the nucleic acid construct produces comprises the two polypeptides joined by a cleavage site(s). The cleavage site may be self-cleaving, such that when the polypeptide is produced, it is immediately cleaved into individual peptides without the need for any external cleavage activity.

The cleavage site may be any sequence which enables the two polypeptides to become separated.

The term "cleavage" is used herein for convenience, but the cleavage site may cause the peptides to separate into individual entities by a mechanism other than classical cleavage. For example, for the Foot-and-Mouth disease virus (FMDV) 2A self-cleaving peptide (see below), various models have been proposed for to account for the "cleavage" activity: proteolysis by a host-cell proteinase, autoproteolysis or a translational effect (Donnelly et al (2001) J. Gen. Virol. 82:1027-1041). The exact mechanism of such "cleavage" is not important for the purposes of the present invention, as long as the cleavage site, when positioned between nucleic acid sequences which encode proteins, causes the proteins to be expressed as separate entities. The cleavage site may be a furin cleavage site.

Furin is an enzyme which belongs to the subtilisin-like proprotein convertase family. The members of this family are proprotein convertases that process latent precursor proteins into their biologically active products. Furin is a calcium-dependent serine endoprotease that can efficiently cleave precursor proteins at their paired basic amino acid processing sites. Examples of furin substrates include proparathyroid hormone, transforming growth factor beta 1 precursor, proalbumin, pro-beta-secretase, membrane type-1 matrix metalloproteinase, beta subunit of pro-nerve growth factor and von Willebrand factor. Furin cleaves proteins just downstream of a basic amino acid target sequence (canonically, Arg-X-(Arg/Lys)-Arg') and is enriched in the Golgi apparatus.

The cleavage site may be a Tobacco Etch Virus (TEV) cleavage site.

TEV protease is a highly sequence-specific cysteine protease which is chymotrypsin-like proteases. It is very specific for its target cleavage site and is therefore frequently used for the controlled cleavage of fusion proteins both in vitro and in vivo. The consensus TEV cleavage site is ENLYFQ\S (where '\' denotes the cleaved peptide bond). Mammalian cells, such as human cells, do not express TEV protease. Thus in embodiments in which the present nucleic acid construct comprises a TEV cleavage site and is expressed in a mammalian cell—exogenous TEV protease must also expressed in the mammalian cell.

The cleavage site may encode a self-cleaving peptide.

A 'self-cleaving peptide' refers to a peptide which functions such that when the polypeptide comprising the proteins and the self-cleaving peptide is produced, it is immediately "cleaved" or separated into distinct and discrete first and second polypeptides without the need for any external cleavage activity.

The self-cleaving peptide may be a 2A self-cleaving peptide from an aphtho- or a cardiovirus. The primary 2A/2B cleavage of the aptho- and cardioviruses is mediated by 2A "cleaving" at its own C-terminus. In apthoviruses, such as foot-and-mouth disease viruses (FMDV) and equine rhinitis A virus, the 2A region is a short section of about 18 amino acids, which, together with the N-terminal residue of protein 2B (a conserved proline residue) represents an autonomous element capable of mediating "cleavage" at its own C-terminus (Donelly et al (2001) as above).

"2A-like" sequences have been found in picornaviruses other than aptho- or cardioviruses, 'picornavirus-like' insect viruses, type C rotaviruses and repeated sequences within *Trypanosoma* spp and a bacterial sequence (Donnelly et al., 2001) as above.

The co-expressing sequence may be an internal ribosome entry sequence (IRES). The co-expressing sequence may be an internal promoter.

Vector

The present invention also provides a vector, or kit of vectors which comprises one or more nucleic acid sequence(s) or nucleic acid construct(s) of the invention. Such a vector may be used to introduce the nucleic acid sequence(s) or construct(s) into a host cell so that it expresses a CAR or CAR component and optionally an agent which modulates CAR activity.

The vector may, for example, be a plasmid or a viral vector, such as a retroviral vector or a lentiviral vector, or a transposon based vector or synthetic mRNA.

The vector may be capable of transfecting or transducing a cell.

Pharmaceutical Composition

The present invention also relates to a pharmaceutical composition containing a plurality of cells, a nucleic acid construct, a first nucleic acid sequence and a second nucleic acid sequence; a vector or a first and a second vector of the present invention. In particular, the invention relates to a pharmaceutical composition containing a plurality of cells according to the present invention.

The pharmaceutical composition may additionally comprise a pharmaceutically acceptable carrier, diluent or excipient. The pharmaceutical composition may optionally comprise one or more further pharmaceutically active polypeptides and/or compounds. Such a formulation may, for example, be in a form suitable for intravenous infusion.

Method of Treatment

The present invention provides a method for treating and/or preventing a disease which comprises the step of administering the cells of the present invention (for example in a pharmaceutical composition as described above) to a subject.

A method for treating a disease relates to the therapeutic use of the cells of the present invention. In this respect, the cells may be administered to a subject having an existing disease or condition in order to lessen, reduce or improve at least one symptom associated with the disease and/or to slow down, reduce or block the progression of the disease.

The method for preventing a disease relates to the prophylactic use of the cells of the present invention. In this respect, the cells may be administered to a subject who has not yet contracted the disease and/or who is not showing any symptoms of the disease to prevent or impair the cause of the disease or to reduce or prevent development of at least one symptom associated with the disease. The subject may have a predisposition for, or be thought to be at risk of developing, the disease.

The method may involve the steps of:
(i) isolating a cell-containing sample;
(ii) transducing or transfecting such cells with a nucleic acid sequence or vector provided by the present invention;
(iii) administering the cells from (ii) to a subject.

The present invention provides a cell, a nucleic acid construct, a first nucleic acid sequence and a second nucleic acid sequence, a vector, or a first and a second vector of the present invention for use in treating and/or preventing a disease. In particular the present invention provides a cell of the present invention for use in treating and/or preventing a disease The invention also relates to the use of a cell, a nucleic acid construct, a first nucleic acid sequence and a second nucleic acid sequence, a vector, or a first and a second vector of the present invention of the present invention in the manufacture of a medicament for the treatment and/or prevention of a disease. In particular, the invention relates to the use of a cell in the manufacture of a medicament for the treatment and/or prevention of a disease The disease to be treated and/or prevented by the method of the present invention may be immune rejection of the cell which comprises (i) a chimeric antigen receptor (CAR) or a transgenic TCR; and (ii) a polypeptide capable of co-localizing a beta-2 microglobulin component of a MHC class I molecule with an intracellular signalling domain.

The disease may be immune rejection of autologous cells or immune rejection of allogenic cells encoding a CAR or transgenic TCR as described herein.

The disease to be treated and/or prevented by the methods of the present invention may be an infection, such as a viral infection.

The methods of the invention may also be for the control of pathogenic immune responses, for example in autoimmune diseases, allergies and graft-vs-host rejection.

The methods may be for the treatment of a cancerous disease, such as bladder cancer, breast cancer, colon cancer, endometrial cancer, kidney cancer (renal cell), leukaemia, lung cancer, melanoma, non-Hodgkin lymphoma, pancreatic cancer, prostate cancer and thyroid cancer.

The CAR cells of the present invention may be capable of killing target cells, such as cancer cells. The target cell may be recognisable by expression of a TAA, for example the expression of a TAA provided above in Table 1.

Method of Making a Cell

CAR or transgenic TCR-expressing cells of the present invention may be generated by introducing DNA or RNA coding for the CAR or TCR and the polypeptide capable of co-localizing a beta-2 microglobulin component of a MHC class I molecule with an intracellular signalling domain within the cell by one of many means including transduction with a viral vector, transfection with DNA or RNA.

The cell of the invention may be made by:
(i) isolation of a cell-containing sample from a subject or one of the other sources listed above; and
(ii) transduction or transfection of the cells with one or more a nucleic acid sequence(s) or nucleic acid construct as defined above in vitro or ex vivo.

The cells may then by purified, for example, selected on the basis of expression of the antigen-binding domain of the antigen-binding polypeptide.

This disclosure is not limited by the exemplary methods and materials disclosed herein, and any methods and materials similar or equivalent to those described herein can be used in the practice or testing of embodiments of this disclosure. Numeric ranges are inclusive of the numbers defining the range. Unless otherwise indicated, any nucleic acid sequences are written left to right in 5' to 3' orientation; amino acid sequences are written left to right in amino to carboxy orientation, respectively.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within this disclosure. The upper and lower limits of these smaller ranges may independently be included or excluded in the range, and each range where either, neither or both limits are included in the smaller ranges is also encompassed within this disclosure, subject to any specifically excluded limit in the stated range. Where the stated range includes one or both of the limits, ranges excluding either or both of those included limits are also included in this disclosure.

It must be noted that as used herein and in the appended claims, the singular forms "a", "an", and "the" include plural referents unless the context clearly dictates otherwise.

The terms "comprising", "comprises" and "comprised of" as used herein are synonymous with "including", "includes" or "containing", "contains", and are inclusive or open-ended and do not exclude additional, non-recited members, elements or method steps. The terms "comprising", "comprises" and "comprised of" also include the term "consisting of".

The publications discussed herein are provided solely for their disclosure prior to the filing date of the present application. Nothing herein is to be construed as an admission that such publications constitute prior art to the claims appended hereto.

The invention will now be further described by way of Examples, which are meant to serve to assist one of ordinary skill in the art in carrying out the invention and are not intended in any way to limit the scope of the invention.

EXAMPLES

Example 1

Demonstration of Reduced Allo-Reactivity in a Mixed Lymphocyte Response Assay

Mixed Lymphocyte response (MLR) assays are classical assays which are used to determine allo-reactivity. Normal donor T-cells are transduced with a retroviral vector which expresses a CD19 CAR co-expressed with B2M-CD3 zeta endodomain (B2M-Z) constructs. T-cells from the same donor are also transduced with a retroviral vector which just expressed the CD19 CAR. These CAR T-cells or CAR/B2M-Z T-cells are irradiated and repeatedly co-cultured with T-cells from another normal donor who is MHC mismatched. The mismatched T-cells are loaded with tritium which allows counting in response to allo-antigens. After repeated co-culture, the CAR T-cells will have greater allo-responses compared with the CAR/B2M-Z T-cells.

Example 2

Demonstration of Reduced Immunogenicity in an Immunocompetent Animal Model

A CAR T-cell cassette is generated which is particularly immunogenic by co-expression of an immunogenic factor such as OVA protein or HSV-TK. In a second CAR T-cell cassette the identical CAR and immunogenic protein are co-expressed along with B2M-Z. Murine splenocytes are transduced with above constructs. Syngeneic mice are conditioned with low-dose total body irradiation and transduced splenocytes are infused. Engraftment and persistence of CAR T-cells is determined by flow cytometry. Immune responses to the immunogenic factor are determined by ELISPOT. Inclusion of the B2M-Z component is expected to enhance engraftment and reduce immune-responses.

Example 3

Demonstration of Reduced Allogeneic Response in a Haploidentical Transfer Model

BALB/C BLACK6 mice are crossed to result in an F1 hybrid. Engraftment of T-cells from an F1 hybrid mouse would normally result in their rejection after administration to a BalB/C mouse due to recognition of BalB/C MHC molecules. F1 CAR T-cells expressing anti murine CD19, and F1 CAR T-cells expressing both anti-murine CD19 CAR as well as B2MZ are administered to a BalB/C mouse after low-dose total body irradiation. Engraftment is studied serially by bioluminescence imaging and after termination by flow-cytometry.

Example 4

Figure 4:
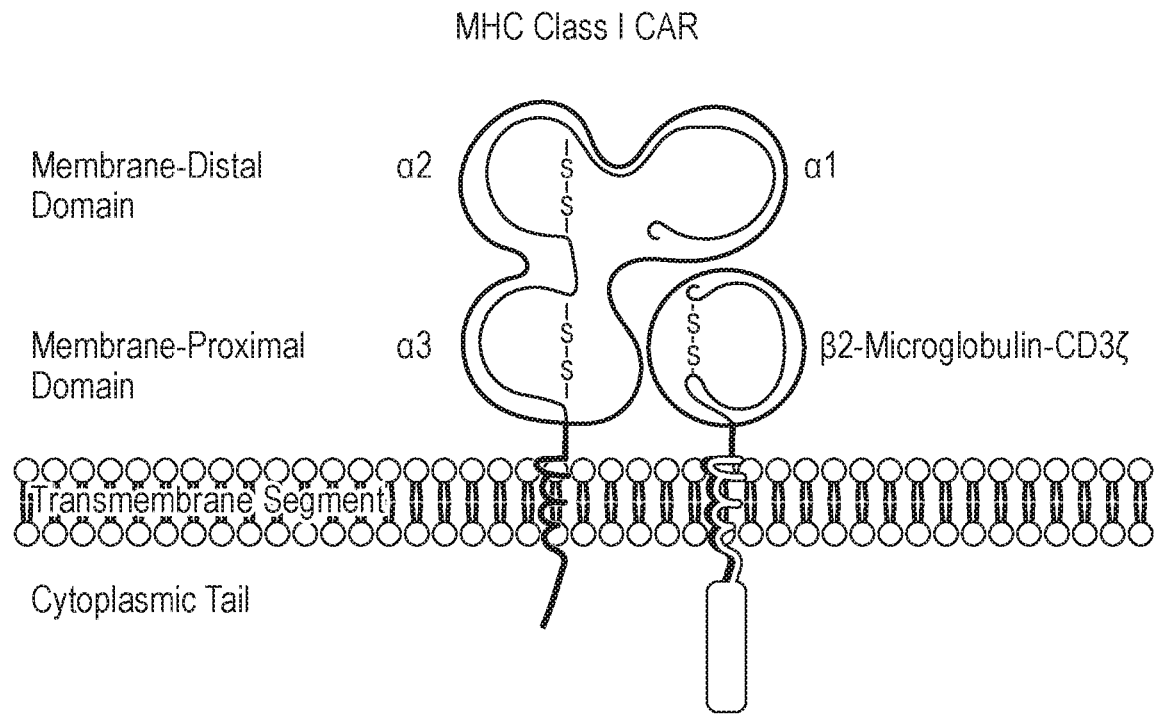
FIG. 4—Schematic diagram illustrating the MHC Class I CAR

Expression of β2m Chimeric Constructs in T Cells Turns MHC I into a Functional CAR MHC Class I molecule is a heterodimer composed of the α chain and β2-microglobulin. In the endogenous MHC I complex, only the α chain is anchored in the cell membrane while β2-microglobulin is non-covalently bound to its partner. The membrane-distal domains of the α chain (α1 and α2) form a grove which binds short peptides that may be recognised by peptide-specific T-cell receptors (TCRs) on the T cells. In contrast to endogenous molecule, MHC I CAR is composed of β2-microglobulin anchored to the cell membrane via a transmembrane domain and linked to a signalling endodomain (FIG. 4). Three possible MHC I CAR designs are possible depending on the design of β2m chimeric constructs (FIG. 5). These constructs may contain CD3ζ endodomain only (1st generation) or may additionally contain co-stimulatory domain, 41BB or CD28 (2nd generation).

To test the functionality of the three β2m chimeric constructs, retroviruses were produced by transient transfection of 293T cells with plasmids encoding the CARs, gag/pol and the envelope protein RD114. After 3 days the supernatants were harvested and used to transduce PBMCs from two healthy donors using retronectin-coated plates. Five days post-transduction CAR-expression was confirmed by flow cytometry.

Both of the PBMC donors used were previously haplotyped as HLA-A02+ by a DNA sequencing method. As previously published, HLA-A02+ donors are capable of binding the HA1H peptide to their peptide-binding grove of the MHC I complex. Thus, a short incubation of the CAR-T cells or non-transduced control cells (NT) obtained from these donors with a recombinant HA1H peptide results in the presentation of the peptide to T cells. CAR-Ts pulsed with a range of HA1H peptide concentrations (0.01-10 μM) were co-cultured in a 2:1 ratio with SupT1 cells engineered to express HA1H-specific TCR. Target cell killing was assayed after two days by flow cytometry and the HA1H peptide EC50 was calculated for each CART using GraphPad Prism (FIG. 6). Simultaneously, the supernatants were removed and cytokine levels were assayed by Luminex Multiplex assay (FIG. 7).

All publications mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

The invention claimed is:

1. A cell which comprises: (i) a chimeric antigen receptor (CAR) or a transgenic T-cell receptor (TCR), and (ii) a polypeptide capable of co-localizing a beta-2 microglobulin (B2M) component of a major histocompatibility complex (MHC) class I molecule with an intracellular signalling domain within the cell, wherein the polypeptide comprises: (a) a B2M component fused to a transmembrane domain and a CD3 zeta endodomain, (b) a B2M component linked to a component of the CD3/TCR complex, or (c) a B2M-TCR bispecific construct comprising a first binding component which recognizes B2M and a second binding component which recognizes the CD3/TCR complex, and wherein the intracellular signalling domain comprises a CD3 zeta endodomain.

2. A cell according to claim 1, wherein the polypeptide comprises a B2M component fused to a transmembrane domain and a CD3 zeta endodomain.

3. A cell according to claim 1, wherein the polypeptide comprises a B2M component linked to a component of the CD3/TCR complex.

4. A cell according to claim 1, wherein the polypeptide comprises a B2M-TCR bispecific construct comprising a first binding component which recognizes B2M and a second binding component which recognizes the CD3/TCR complex.

5. A nucleic acid construct formulated for being introduced into a cell which comprises: (i) a first nucleic acid sequence which encodes a chimeric antigen receptor (CAR) or a transgenic TCR; and (ii) a second nucleic acid sequence which encodes a polypeptide capable of co-localizing a beta-2 microglobulin (B2M) component of a major histocompatibility complex (MHC) class I molecule with an intracellular signalling domain, wherein the polypeptide comprises: (a) a B2M component fused to a transmembrane domain and a CD3 zeta endodomain, (b) a B2M component linked to a component of the CD3/TCR complex, or (c) a B2M-TCR bispecific construct comprising a first binding component which recognizes the B2M and a second binding component which recognizes the CD3/TCR complex, and wherein the intracellular signalling domain comprises a CD3 zeta endodomain.

6. A vector which comprises a nucleic acid construct according to claim 5.

7. A kit comprising the vector of claim 6.

8. A pharmaceutical composition which comprises a plurality of cells according to claim 1.

9. A method for treating and/or preventing a disease, which comprises the step of administering a pharmaceutical composition according to claim 8 to a subject in need thereof.

10. The method according to claim 9 wherein the cell is autologous.

11. The method according to claim 9 wherein the cell is allogenic.

12. The method according to claim 9, wherein the disease is immune rejection of the cell.

13. A method for making a cell according to claim 1, which comprises the step of introducing into the cell: (i) a first nucleic acid sequence which encodes the chimeric antigen receptor (CAR) or the transgenic TCR; and (ii) a second nucleic acid sequence which encodes the polypeptide.

\* \* \* \* \*

SEQUENCE LISTING

```
<160> NUMBER OF SEQ ID NOS: 45

<210> SEQ ID NO 1
<211> LENGTH: 119
<212> TYPE: PRT
<213> ORGANISM: Artificial Sequence
<220> FEATURE:
<223> OTHER INFORMATION: B2M amino acid sequence

<400> SEQUENCE: 1

Met Ser Arg Ser Val Ala Leu Ala Val Leu Ala Leu Leu Ser Leu Ser
1               5                   10                  15

Gly Leu Glu Ala Ile Gln Arg Thr Pro Lys Ile Gln Val Tyr Ser Arg
            20                  25                  30

His Pro Ala Glu Asn Gly Lys Ser Asn Phe Leu Asn Cys Tyr Val Ser
        35                  40                  45

Gly Phe His Pro Ser Asp Ile Glu Val Asp Leu Leu Lys Asn Gly Glu
    50                  55                  60

Arg Ile Glu Lys Val Glu His Ser Asp Leu Ser Phe Ser Lys Asp Trp
65                  70                  75                  80

Ser Phe Tyr Leu Leu Tyr Tyr Thr Glu Phe Thr Pro Thr Glu Lys Asp
                85                  90                  95

Glu Tyr Ala Cys Arg Val Asn His Val Thr Leu Ser Gln Pro Lys Ile
            100                 105                 110

Val Lys Trp Asp Arg Asp Met
        115

<210> SEQ ID NO 2
<211> LENGTH: 28
<212> TYPE: PRT
<213> ORGANISM: Artificial Sequence
<220> FEATURE:
<223> OTHER INFORMATION: CD28 transmembrane domain

<400> SEQUENCE: 2

Phe Trp Val Leu Val Val Val Gly Gly Val Leu Ala Cys Tyr Ser Leu
1               5                   10                  15

Leu Val Thr Val Ala Phe Ile Ile Phe Trp Val Arg
            20                  25

<210> SEQ ID NO 3
<211> LENGTH: 251
```

```
<212> TYPE: PRT
<213> ORGANISM: Artificial Sequence
<220> FEATURE:
<223> OTHER INFORMATION: engineered B2M sequence

<400> SEQUENCE: 3
```

| | | | | | | | | | | | | | | | |
|---|---|---|---|---|---|---|---|---|---|---|---|---|---|---|---|
| Met | Ser | Arg | Ser | Val | Ala | Leu | Ala | Val | Leu | Ala | Leu | Leu | Ser | Leu | Ser |
| 1 | | | | 5 | | | | | 10 | | | | | 15 | |
| Gly | Leu | Glu | Ala | Ile | Gln | Arg | Thr | Pro | Lys | Ile | Gln | Val | Tyr | Ser | Arg |
| | | | 20 | | | | | 25 | | | | | 30 | | |
| His | Pro | Ala | Glu | Asn | Gly | Lys | Ser | Asn | Phe | Leu | Asn | Cys | Tyr | Val | Ser |
| | | 35 | | | | | 40 | | | | | 45 | | | |
| Gly | Phe | His | Pro | Ser | Asp | Ile | Glu | Val | Asp | Leu | Leu | Lys | Asn | Gly | Glu |
| | 50 | | | | | 55 | | | | | 60 | | | | |
| Arg | Ile | Glu | Lys | Val | Glu | His | Ser | Asp | Leu | Ser | Phe | Ser | Lys | Asp | Trp |
| 65 | | | | | 70 | | | | | 75 | | | | | 80 |
| Ser | Phe | Tyr | Leu | Leu | Tyr | Tyr | Thr | Glu | Phe | Thr | Pro | Thr | Glu | Lys | Asp |
| | | | | 85 | | | | | 90 | | | | | 95 | |
| Glu | Tyr | Ala | Cys | Arg | Val | Asn | His | Val | Thr | Leu | Ser | Gln | Pro | Lys | Ile |
| | | | 100 | | | | | 105 | | | | | 110 | | |
| Val | Lys | Trp | Asp | Arg | Asp | Met | Ile | Tyr | Ile | Trp | Ala | Pro | Leu | Ala | Gly |
| | | 115 | | | | | 120 | | | | | 125 | | | |
| Thr | Cys | Gly | Val | Leu | Leu | Leu | Ser | Leu | Val | Ile | Thr | Leu | Tyr | Ser | Arg |
| | 130 | | | | | 135 | | | | | 140 | | | | |
| Ser | Ala | Asp | Ala | Pro | Ala | Tyr | Gln | Gln | Gly | Gln | Asn | Gln | Leu | Tyr | Asn |
| 145 | | | | | 150 | | | | | 155 | | | | | 160 |
| Glu | Leu | Asn | Leu | Gly | Arg | Arg | Glu | Glu | Tyr | Asp | Val | Leu | Asp | Lys | Arg |
| | | | | 165 | | | | | 170 | | | | | 175 | |
| Arg | Gly | Arg | Asp | Pro | Glu | Met | Gly | Gly | Lys | Pro | Gln | Arg | Arg | Lys | Asn |
| | | | 180 | | | | | 185 | | | | | 190 | | |
| Pro | Gln | Glu | Gly | Leu | Tyr | Asn | Glu | Leu | Gln | Lys | Asp | Lys | Met | Ala | Glu |
| | | | | 195 | | | | | 200 | | | | | 205 | |
| Ala | Tyr | Ser | Glu | Ile | Gly | Met | Lys | Gly | Glu | Arg | Arg | Arg | Gly | Lys | Gly |
| | | 210 | | | | | 215 | | | | | 220 | | | |
| His | Asp | Gly | Leu | Tyr | Gln | Gly | Leu | Ser | Thr | Ala | Thr | Lys | Asp | Thr | Tyr |
| 225 | | | | | 230 | | | | | 235 | | | | | 240 |
| Asp | Ala | Leu | His | Met | Gln | Ala | Leu | Pro | Pro | Arg | | | | | |
| | | | | 245 | | | | | 250 | | | | | | |

```
<210> SEQ ID NO 4
<211> LENGTH: 164
<212> TYPE: PRT
<213> ORGANISM: Artificial Sequence
<220> FEATURE:
<223> OTHER INFORMATION: example human CD3zeta sequence

<400> SEQUENCE: 4
```

| | | | | | | | | | | | | | | | |
|---|---|---|---|---|---|---|---|---|---|---|---|---|---|---|---|
| Met | Lys | Trp | Lys | Ala | Leu | Phe | Thr | Ala | Ala | Ile | Leu | Gln | Ala | Gln | Leu |
| 1 | | | | 5 | | | | | 10 | | | | | 15 | |
| Pro | Ile | Thr | Glu | Ala | Gln | Ser | Phe | Gly | Leu | Leu | Asp | Pro | Lys | Leu | Cys |
| | | | 20 | | | | | 25 | | | | | 30 | | |
| Tyr | Leu | Leu | Asp | Gly | Ile | Leu | Phe | Ile | Tyr | Gly | Val | Ile | Leu | Thr | Ala |
| | | | | 35 | | | | | 40 | | | | | 45 | |
| Leu | Phe | Leu | Arg | Val | Lys | Phe | Ser | Arg | Ser | Ala | Asp | Ala | Pro | Ala | Tyr |
| | 50 | | | | | 55 | | | | | 60 | | | | |
| Gln | Gln | Gly | Gln | Asn | Gln | Leu | Tyr | Asn | Glu | Leu | Asn | Leu | Gly | Arg | Arg |
| 65 | | | | | 70 | | | | | 75 | | | | | 80 |

Glu Glu Tyr Asp Val Leu Asp Lys Arg Arg Gly Arg Asp Pro Glu Met
                85                  90                  95

Gly Gly Lys Pro Gln Arg Arg Lys Asn Pro Gln Glu Gly Leu Tyr Asn
            100                 105                 110

Glu Leu Gln Lys Asp Lys Met Ala Glu Ala Tyr Ser Glu Ile Gly Met
        115                 120                 125

Lys Gly Glu Arg Arg Arg Gly Lys Gly His Asp Gly Leu Tyr Gln Gly
    130                 135                 140

Leu Ser Thr Ala Thr Lys Asp Thr Tyr Asp Ala Leu His Met Gln Ala
145                 150                 155                 160

Leu Pro Pro Arg

<210> SEQ ID NO 5
<211> LENGTH: 182
<212> TYPE: PRT
<213> ORGANISM: Artificial Sequence
<220> FEATURE:
<223> OTHER INFORMATION: example human CD3gamma sequence

<400> SEQUENCE: 5

Met Glu Gln Gly Lys Gly Leu Ala Val Leu Ile Leu Ala Ile Ile Leu
1               5                   10                  15

Leu Gln Gly Thr Leu Ala Gln Ser Ile Lys Gly Asn His Leu Val Lys
            20                  25                  30

Val Tyr Asp Tyr Gln Glu Asp Gly Ser Val Leu Leu Thr Cys Asp Ala
        35                  40                  45

Glu Ala Lys Asn Ile Thr Trp Phe Lys Asp Gly Lys Met Ile Gly Phe
    50                  55                  60

Leu Thr Glu Asp Lys Lys Lys Trp Asn Leu Gly Ser Asn Ala Lys Asp
65                  70                  75                  80

Pro Arg Gly Met Tyr Gln Cys Lys Gly Ser Gln Asn Lys Ser Lys Pro
                85                  90                  95

Leu Gln Val Tyr Tyr Arg Met Cys Gln Asn Cys Ile Glu Leu Asn Ala
            100                 105                 110

Ala Thr Ile Ser Gly Phe Leu Phe Ala Glu Ile Val Ser Ile Phe Val
        115                 120                 125

Leu Ala Val Gly Val Tyr Phe Ile Ala Gly Gln Asp Gly Val Arg Gln
    130                 135                 140

Ser Arg Ala Ser Asp Lys Gln Thr Leu Leu Pro Asn Asp Gln Leu Tyr
145                 150                 155                 160

Gln Pro Leu Lys Asp Arg Glu Asp Asp Gln Tyr Ser His Leu Gln Gly
                165                 170                 175

Asn Gln Leu Arg Arg Asn
            180

<210> SEQ ID NO 6
<211> LENGTH: 171
<212> TYPE: PRT
<213> ORGANISM: Artificial Sequence
<220> FEATURE:
<223> OTHER INFORMATION: example human CD3delta sequence

<400> SEQUENCE: 6

Met Glu His Ser Thr Phe Leu Ser Gly Leu Val Leu Ala Thr Leu Leu
1               5                   10                  15

Ser Gln Val Ser Pro Phe Lys Ile Pro Ile Glu Glu Leu Glu Asp Arg
            20                  25                  30

Val Phe Val Asn Cys Asn Thr Ser Ile Thr Trp Val Glu Gly Thr Val
            35                  40                  45

Gly Thr Leu Leu Ser Asp Ile Thr Arg Leu Asp Leu Gly Lys Arg Ile
    50                  55                  60

Leu Asp Pro Arg Gly Ile Tyr Arg Cys Asn Gly Thr Asp Ile Tyr Lys
65                  70                  75                  80

Asp Lys Glu Ser Thr Val Gln Val His Tyr Arg Met Cys Gln Ser Cys
                85                  90                  95

Val Glu Leu Asp Pro Ala Thr Val Ala Gly Ile Ile Val Thr Asp Val
            100                 105                 110

Ile Ala Thr Leu Leu Leu Ala Leu Gly Val Phe Cys Phe Ala Gly His
        115                 120                 125

Glu Thr Gly Arg Leu Ser Gly Ala Ala Asp Thr Gln Ala Leu Leu Arg
    130                 135                 140

Asn Asp Gln Val Tyr Gln Pro Leu Arg Asp Arg Asp Asp Ala Gln Tyr
145                 150                 155                 160

Ser His Leu Gly Gly Asn Trp Ala Arg Asn Lys
                165                 170

<210> SEQ ID NO 7
<211> LENGTH: 207
<212> TYPE: PRT
<213> ORGANISM: Artificial Sequence
<220> FEATURE:
<223> OTHER INFORMATION: example human CD3epsilon sequence

<400> SEQUENCE: 7

Met Gln Ser Gly Thr His Trp Arg Val Leu Gly Leu Cys Leu Leu Ser
1               5                   10                  15

Val Gly Val Trp Gly Gln Asp Gly Asn Glu Glu Met Gly Gly Ile Thr
            20                  25                  30

Gln Thr Pro Tyr Lys Val Ser Ile Ser Gly Thr Thr Val Ile Leu Thr
        35                  40                  45

Cys Pro Gln Tyr Pro Gly Ser Glu Ile Leu Trp Gln His Asn Asp Lys
    50                  55                  60

Asn Ile Gly Gly Asp Glu Asp Asp Lys Asn Ile Gly Ser Asp Glu Asp
65                  70                  75                  80

His Leu Ser Leu Lys Glu Phe Ser Glu Leu Glu Gln Ser Gly Tyr Tyr
                85                  90                  95

Val Cys Tyr Pro Arg Gly Ser Lys Pro Glu Asp Ala Asn Phe Tyr Leu
            100                 105                 110

Tyr Leu Arg Ala Arg Val Cys Glu Asn Cys Met Glu Met Asp Val Met
        115                 120                 125

Ser Val Ala Thr Ile Val Ile Val Asp Ile Cys Ile Thr Gly Gly Leu
    130                 135                 140

Leu Leu Leu Val Tyr Tyr Trp Ser Lys Asn Arg Lys Ala Lys Ala Lys
145                 150                 155                 160

Pro Val Thr Arg Gly Ala Gly Ala Gly Gly Arg Gln Arg Gly Gln Asn
                165                 170                 175

Lys Glu Arg Pro Pro Pro Val Pro Asn Pro Asp Tyr Glu Pro Ile Arg
            180                 185                 190

Lys Gly Gln Arg Asp Leu Tyr Ser Gly Leu Asn Gln Arg Arg Ile
        195                 200                 205

<210> SEQ ID NO 8

```
<211> LENGTH: 16
<212> TYPE: PRT
<213> ORGANISM: Artificial Sequence
<220> FEATURE:
<223> OTHER INFORMATION: linker peptide

<400> SEQUENCE: 8

Ser Gly Gly Gly Gly Ser Gly Gly Gly Gly Ser Gly Gly Gly Gly Ser
1               5                   10                  15

<210> SEQ ID NO 9
<211> LENGTH: 321
<212> TYPE: PRT
<213> ORGANISM: Artificial Sequence
<220> FEATURE:
<223> OTHER INFORMATION: B2M-CD3epsilon polypeptide

<400> SEQUENCE: 9

Met Ser Arg Ser Val Ala Leu Ala Val Leu Ala Leu Leu Ser Leu Ser
1               5                   10                  15

Gly Leu Glu Ala Ile Gln Arg Thr Pro Lys Ile Gln Val Tyr Ser Arg
                20                  25                  30

His Pro Ala Glu Asn Gly Lys Ser Asn Phe Leu Asn Cys Tyr Val Ser
            35                  40                  45

Gly Phe His Pro Ser Asp Ile Glu Val Asp Leu Leu Lys Asn Gly Glu
        50                  55                  60

Arg Ile Glu Lys Val Glu His Ser Asp Leu Ser Phe Ser Lys Asp Trp
65                  70                  75                  80

Ser Phe Tyr Leu Leu Tyr Tyr Thr Glu Phe Thr Pro Thr Glu Lys Asp
                85                  90                  95

Glu Tyr Ala Cys Arg Val Asn His Val Thr Leu Ser Gln Pro Lys Ile
            100                 105                 110

Val Lys Trp Asp Arg Asp Met Ser Gly Gly Gly Gly Ser Gly Gly Gly
        115                 120                 125

Gly Ser Gly Gly Gly Gly Ser Gln Asp Gly Asn Glu Glu Met Gly Gly
    130                 135                 140

Ile Thr Gln Thr Pro Tyr Lys Val Ser Ile Ser Gly Thr Thr Val Ile
145                 150                 155                 160

Leu Thr Cys Pro Gln Tyr Pro Gly Ser Glu Ile Leu Trp Gln His Asn
                165                 170                 175

Asp Lys Asn Ile Gly Gly Asp Glu Asp Asp Lys Asn Ile Gly Ser Asp
            180                 185                 190

Glu Asp His Leu Ser Leu Lys Glu Phe Ser Glu Leu Glu Gln Ser Gly
        195                 200                 205

Tyr Tyr Val Cys Tyr Pro Arg Gly Ser Lys Pro Glu Asp Ala Asn Phe
    210                 215                 220

Tyr Leu Tyr Leu Arg Ala Arg Val Cys Glu Asn Cys Met Glu Met Asp
225                 230                 235                 240

Val Met Ser Val Ala Thr Ile Val Ile Val Asp Ile Cys Ile Thr Gly
                245                 250                 255

Gly Leu Leu Leu Leu Val Tyr Tyr Trp Ser Lys Asn Arg Lys Ala Lys
            260                 265                 270

Ala Lys Pro Val Thr Arg Gly Ala Gly Ala Gly Gly Arg Gln Arg Gly
        275                 280                 285

Gln Asn Lys Glu Arg Pro Pro Pro Val Pro Asn Pro Asp Tyr Glu Pro
    290                 295                 300

Ile Arg Lys Gly Gln Arg Asp Leu Tyr Ser Gly Leu Asn Gln Arg Arg
```

-continued

```
                305                 310                 315                 320
Ile

<210> SEQ ID NO 10
<211> LENGTH: 278
<212> TYPE: PRT
<213> ORGANISM: Artificial Sequence
<220> FEATURE:
<223> OTHER INFORMATION: B2M-CD3zeta polypeptide

<400> SEQUENCE: 10

Met Ser Arg Ser Val Ala Leu Ala Val Leu Ala Leu Leu Ser Leu Ser
1               5                   10                  15

Gly Leu Glu Ala Ile Gln Arg Thr Pro Lys Ile Gln Val Tyr Ser Arg
            20                  25                  30

His Pro Ala Glu Asn Gly Lys Ser Asn Phe Leu Asn Cys Tyr Val Ser
        35                  40                  45

Gly Phe His Pro Ser Asp Ile Glu Val Asp Leu Leu Lys Asn Gly Glu
    50                  55                  60

Arg Ile Glu Lys Val Glu His Ser Asp Leu Ser Phe Ser Lys Asp Trp
65                  70                  75                  80

Ser Phe Tyr Leu Leu Tyr Tyr Thr Glu Phe Thr Pro Thr Glu Lys Asp
                85                  90                  95

Glu Tyr Ala Cys Arg Val Asn His Val Thr Leu Ser Gln Pro Lys Ile
            100                 105                 110

Val Lys Trp Asp Arg Asp Met Ser Gly Gly Gly Ser Gly Gly Gly
        115                 120                 125

Gly Ser Gly Gly Gly Ser Gln Ser Phe Gly Leu Leu Asp Pro Lys
    130                 135                 140

Leu Cys Tyr Leu Leu Asp Gly Ile Leu Phe Ile Tyr Gly Val Ile Leu
145                 150                 155                 160

Thr Ala Leu Phe Leu Arg Val Lys Phe Ser Arg Ser Ala Asp Ala Pro
                165                 170                 175

Ala Tyr Gln Gln Gly Gln Asn Gln Leu Tyr Asn Glu Leu Asn Leu Gly
            180                 185                 190

Arg Arg Glu Glu Tyr Asp Val Leu Asp Lys Arg Arg Gly Arg Asp Pro
        195                 200                 205

Glu Met Gly Gly Lys Pro Gln Arg Arg Lys Asn Pro Gln Glu Gly Leu
    210                 215                 220

Tyr Asn Glu Leu Gln Lys Asp Lys Met Ala Glu Ala Tyr Ser Glu Ile
225                 230                 235                 240

Gly Met Lys Gly Glu Arg Arg Arg Gly Lys Gly His Asp Gly Leu Tyr
                245                 250                 255

Gln Gly Leu Ser Thr Ala Thr Lys Asp Thr Tyr Asp Ala Leu His Met
            260                 265                 270

Gln Ala Leu Pro Pro Arg
        275

<210> SEQ ID NO 11
<211> LENGTH: 242
<212> TYPE: PRT
<213> ORGANISM: Artificial Sequence
<220> FEATURE:
<223> OTHER INFORMATION: B2Mb binding domain

<400> SEQUENCE: 11

Glu Val Gln Leu Gln Gln Ser Gly Ala Glu Leu Val Lys Pro Gly Ala
```

```
            1               5                   10                  15
        Ser Val Lys Leu Ser Cys Thr Pro Ser Gly Phe Asn Val Lys Asp Thr
                        20                  25                  30

Tyr Ile His Trp Val Lys Gln Arg Pro Lys Gln Gly Leu Glu Trp Ile
                        35                  40                  45

Gly Arg Ile Asp Pro Ser Asp Gly Asp Ile Lys Tyr Asp Pro Lys Phe
                50                  55                  60

Gln Gly Lys Ala Thr Ile Thr Ala Asp Thr Ser Ser Asn Thr Val Ser
        65                  70                  75                  80

Leu Gln Leu Ser Ser Leu Thr Ser Glu Asp Thr Ala Val Tyr Tyr Cys
                        85                  90                  95

Ala Arg Trp Phe Gly Asp Tyr Gly Ala Met Asn Tyr Trp Gly Gln Gly
                        100                 105                 110

Thr Ser Val Thr Val Ser Ser Gly Gly Gly Gly Ser Gly Gly Gly Gly
                        115                 120                 125

Ser Gly Gly Gly Gly Ser Asp Ile Leu Met Thr Gln Ser Pro Ala Ser
                130                 135                 140

Gln Ser Ala Ser Leu Gly Glu Ser Val Thr Ile Thr Cys Leu Ala Ser
        145                 150                 155                 160

Gln Thr Ile Gly Thr Trp Leu Ala Trp Tyr Gln Lys Pro Gly Lys
                        165                 170                 175

Ser Pro Gln Leu Leu Ile Tyr Ala Ala Thr Ser Leu Ala Asp Gly Val
                        180                 185                 190

Pro Ser Arg Phe Ser Gly Ser Gly Ser Gly Thr Lys Phe Ser Leu Lys
                        195                 200                 205

Ile Arg Thr Leu Gln Ala Glu Asp Phe Val Ser Tyr Tyr Cys Gln Gln
                        210                 215                 220

Leu Tyr Ser Lys Pro Tyr Thr Phe Gly Gly Gly Thr Lys Leu Glu Ile
        225                 230                 235                 240

Lys Arg

<210> SEQ ID NO 12
<211> LENGTH: 242
<212> TYPE: PRT
<213> ORGANISM: Artificial Sequence
<220> FEATURE:
<223> OTHER INFORMATION: scFV comprising the CDR sequences from OKT3

<400> SEQUENCE: 12

Gln Val Gln Leu Gln Gln Ser Gly Ala Glu Leu Ala Arg Pro Gly Ala
        1               5                   10                  15

Ser Val Lys Met Ser Cys Lys Ala Ser Gly Tyr Thr Phe Thr Arg Tyr
                        20                  25                  30

Thr Met His Trp Val Lys Gln Arg Pro Gly Gln Gly Leu Glu Trp Ile
                        35                  40                  45

Gly Tyr Ile Asn Pro Ser Arg Gly Tyr Thr Asn Tyr Asn Gln Lys Phe
                50                  55                  60

Lys Asp Lys Ala Thr Leu Thr Thr Asp Lys Ser Ser Ser Thr Ala Tyr
        65                  70                  75                  80

Met Gln Leu Ser Ser Leu Thr Ser Glu Asp Ser Ala Val Tyr Tyr Cys
                        85                  90                  95

Ala Arg Tyr Tyr Asp Asp His Tyr Cys Leu Asp Tyr Trp Gly Gln Gly
                        100                 105                 110

Thr Thr Leu Thr Val Ser Ser Gly Gly Gly Gly Ser Gly Gly Gly Gly
                        115                 120                 125
```

```
Gly Ser Gly Gly Gly Ser Gln Ile Val Leu Thr Gln Ser Pro Ala
    130                 135                 140

Ile Met Ser Ala Ser Pro Gly Glu Lys Val Thr Met Thr Cys Ser Ala
145                 150                 155                 160

Ser Ser Ser Val Ser Tyr Met Asn Trp Tyr Gln Gln Lys Ser Gly Thr
                165                 170                 175

Ser Pro Lys Arg Trp Ile Tyr Asp Thr Ser Lys Leu Ala Ser Gly Val
            180                 185                 190

Pro Ala His Phe Arg Gly Ser Gly Ser Gly Thr Ser Tyr Ser Leu Thr
        195                 200                 205

Ile Ser Gly Met Glu Ala Glu Asp Ala Ala Thr Tyr Tyr Cys Gln Gln
    210                 215                 220

Trp Ser Ser Asn Pro Phe Thr Phe Gly Ser Gly Thr Lys Leu Glu Ile
225                 230                 235                 240

Asn Arg

<210> SEQ ID NO 13
<211> LENGTH: 13
<212> TYPE: PRT
<213> ORGANISM: Artificial Sequence
<220> FEATURE:
<223> OTHER INFORMATION: Heavy chain complementarity determining region
      (CDR), CDR1

<400> SEQUENCE: 13

Lys Ala Ser Gly Tyr Thr Phe Thr Arg Tyr Thr Met His
1               5                   10

<210> SEQ ID NO 14
<211> LENGTH: 16
<212> TYPE: PRT
<213> ORGANISM: Artificial Sequence
<220> FEATURE:
<223> OTHER INFORMATION: Heavy chain CDR2

<400> SEQUENCE: 14

Ile Asn Pro Ser Arg Gly Tyr Thr Asn Tyr Asn Gln Lys Phe Lys Asp
1               5                   10                  15

<210> SEQ ID NO 15
<211> LENGTH: 10
<212> TYPE: PRT
<213> ORGANISM: Artificial Sequence
<220> FEATURE:
<223> OTHER INFORMATION: Heavy chain CDR2

<400> SEQUENCE: 15

Tyr Tyr Asp Asp His Tyr Cys Leu Asp Tyr
1               5                   10

<210> SEQ ID NO 16
<211> LENGTH: 10
<212> TYPE: PRT
<213> ORGANISM: Artificial Sequence
<220> FEATURE:
<223> OTHER INFORMATION: Light chain CDR1

<400> SEQUENCE: 16

Ser Ala Ser Ser Ser Val Ser Tyr Met Asn
1               5                   10

<210> SEQ ID NO 17
```

```
<211> LENGTH: 11
<212> TYPE: PRT
<213> ORGANISM: Artificial Sequence
<220> FEATURE:
<223> OTHER INFORMATION: Light chain CDR2

<400> SEQUENCE: 17

Arg Trp Ile Tyr Asp Thr Ser Lys Leu Ala Ser
1               5                   10

<210> SEQ ID NO 18
<211> LENGTH: 9
<212> TYPE: PRT
<213> ORGANISM: Artificial Sequence
<220> FEATURE:
<223> OTHER INFORMATION: Light chain CDR3

<400> SEQUENCE: 18

Gln Gln Trp Ser Ser Asn Pro Phe Thr
1               5

<210> SEQ ID NO 19
<211> LENGTH: 26
<212> TYPE: PRT
<213> ORGANISM: Artificial Sequence
<220> FEATURE:
<223> OTHER INFORMATION: spacer sequence, IgG1 hinge

<400> SEQUENCE: 19

Ala Glu Pro Lys Ser Pro Asp Lys Thr His Thr Cys Pro Pro Cys Pro
1               5                   10                  15

Lys Asp Pro Lys Ser Gly Gly Gly Gly Ser
            20                  25

<210> SEQ ID NO 20
<211> LENGTH: 45
<212> TYPE: PRT
<213> ORGANISM: Artificial Sequence
<220> FEATURE:
<223> OTHER INFORMATION: spacer sequence, CD8 stalk

<400> SEQUENCE: 20

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp
        35                  40                  45

<210> SEQ ID NO 21
<211> LENGTH: 7
<212> TYPE: PRT
<213> ORGANISM: Artificial Sequence
<220> FEATURE:
<223> OTHER INFORMATION: chain break sequence

<400> SEQUENCE: 21

Ser Gly Gly Gly Ser Asp Pro
1               5

<210> SEQ ID NO 22
<211> LENGTH: 6
<212> TYPE: PRT
<213> ORGANISM: Artificial Sequence
<220> FEATURE:
<223> OTHER INFORMATION: serine-glycine linker
```

<400> SEQUENCE: 22

Ser Gly Gly Gly Gly Ser
1               5

<210> SEQ ID NO 23
<211> LENGTH: 575
<212> TYPE: PRT
<213> ORGANISM: Artificial Sequence
<220> FEATURE:
<223> OTHER INFORMATION: bispecific molecule, comprises a B2M-binding
      domain linked to a CD3-binding and a transmembrane domain

<400> SEQUENCE: 23

Met Glu Thr Asp Thr Leu Leu Leu Trp Val Leu Leu Leu Trp Val Pro
1               5                   10                  15

Gly Ser Thr Gly Glu Val Gln Leu Gln Gln Ser Gly Ala Glu Leu Val
            20                  25                  30

Lys Pro Gly Ala Ser Val Lys Leu Ser Cys Thr Pro Ser Gly Phe Asn
        35                  40                  45

Val Lys Asp Thr Tyr Ile His Trp Val Lys Gln Arg Pro Lys Gln Gly
    50                  55                  60

Leu Glu Trp Ile Gly Arg Ile Asp Pro Ser Asp Gly Asp Ile Lys Tyr
65                  70                  75                  80

Asp Pro Lys Phe Gln Gly Lys Ala Thr Ile Thr Ala Asp Thr Ser Ser
                85                  90                  95

Asn Thr Val Ser Leu Gln Leu Ser Ser Leu Thr Ser Glu Asp Thr Ala
            100                 105                 110

Val Tyr Tyr Cys Ala Arg Trp Phe Gly Asp Tyr Gly Ala Met Asn Tyr
        115                 120                 125

Trp Gly Gln Gly Thr Ser Val Thr Val Ser Ser Gly Gly Gly Gly Ser
    130                 135                 140

Gly Gly Gly Gly Ser Gly Gly Gly Ser Asp Ile Leu Met Thr Gln
145                 150                 155                 160

Ser Pro Ala Ser Gln Ser Ala Ser Leu Gly Glu Ser Val Thr Ile Thr
                165                 170                 175

Cys Leu Ala Ser Gln Thr Ile Gly Thr Trp Leu Ala Trp Tyr Gln Gln
            180                 185                 190

Lys Pro Gly Lys Ser Pro Gln Leu Leu Ile Tyr Ala Ala Thr Ser Leu
        195                 200                 205

Ala Asp Gly Val Pro Ser Arg Phe Ser Gly Ser Gly Ser Gly Thr Lys
    210                 215                 220

Phe Ser Leu Lys Ile Arg Thr Leu Gln Ala Glu Asp Phe Val Ser Tyr
225                 230                 235                 240

Tyr Cys Gln Gln Leu Tyr Ser Lys Pro Tyr Thr Phe Gly Gly Gly Thr
                245                 250                 255

Lys Leu Glu Ile Lys Arg Ser Gly Gly Gly Gly Ser Gly Gly Gly Gly
            260                 265                 270

Ser Gly Gly Gly Gly Ser Gln Ile Val Leu Thr Gln Ser Pro Ala Ile
        275                 280                 285

Met Ser Ala Ser Pro Gly Glu Lys Val Thr Met Thr Cys Ser Ala Ser
    290                 295                 300

Ser Ser Val Ser Tyr Met Asn Trp Tyr Gln Gln Lys Ser Gly Thr Ser
305                 310                 315                 320

Pro Lys Arg Trp Ile Tyr Asp Thr Ser Lys Leu Ala Ser Gly Val Pro
                325                 330                 335

```
Ala His Phe Arg Gly Ser Gly Ser Gly Thr Ser Tyr Ser Leu Thr Ile
                340                 345                 350

Ser Gly Met Glu Ala Glu Asp Ala Ala Thr Tyr Tyr Cys Gln Gln Trp
            355                 360                 365

Ser Ser Asn Pro Phe Thr Phe Gly Ser Gly Thr Lys Leu Glu Ile Asn
        370                 375                 380

Arg Ser Ser Ser Gly Gly Gly Ser Gly Gly Gly Ser Gly Gly Gly Ser Gly Gly
385                 390                 395                 400

Gly Gly Ser Gln Val Gln Leu Gln Gln Ser Gly Ala Glu Leu Ala Arg
            405                 410                 415

Pro Gly Ala Ser Val Lys Met Ser Cys Lys Ala Ser Gly Tyr Thr Phe
            420                 425                 430

Thr Arg Tyr Thr Met His Trp Val Lys Gln Arg Pro Gly Gln Gly Leu
            435                 440                 445

Glu Trp Ile Gly Tyr Ile Asn Pro Ser Arg Gly Tyr Thr Asn Tyr Asn
450                 455                 460

Gln Lys Phe Lys Asp Lys Ala Thr Leu Thr Thr Asp Lys Ser Ser Ser
465                 470                 475                 480

Thr Ala Tyr Met Gln Leu Ser Ser Leu Thr Ser Glu Asp Ser Ala Val
            485                 490                 495

Tyr Tyr Cys Ala Arg Tyr Tyr Asp Asp His Tyr Cys Leu Asp Tyr Trp
            500                 505                 510

Gly Gln Gly Thr Thr Leu Thr Val Ser Ser Gly Gly Gly Gly Ser
            515                 520                 525

Gly Gly Gly Gly Ser Gly Gly Gly Ser Ile Tyr Ile Trp Ala Pro
            530                 535                 540

Leu Ala Thr Cys Gly Val Leu Leu Leu Ser Leu Val Ile Thr Leu Tyr
545                 550                 555                 560

Cys Asn His Arg Asn Arg Arg Val Cys Lys Cys Pro Arg Pro
                565                 570                 575

<210> SEQ ID NO 24
<211> LENGTH: 112
<212> TYPE: PRT
<213> ORGANISM: Artificial Sequence
<220> FEATURE:
<223> OTHER INFORMATION: CD3-zeta endodomain

<400> SEQUENCE: 24

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 25
```

<211> LENGTH: 368
<212> TYPE: PRT
<213> ORGANISM: Artificial Sequence
<220> FEATURE:
<223> OTHER INFORMATION: 4-1BB and CD3-zeta endodomains

<400> SEQUENCE: 25

```
Met Gly Asn Ser Cys Tyr Asn Ile Val Ala Thr Leu Leu Leu Val Leu
1               5                   10                  15

Asn Phe Glu Arg Thr Arg Ser Leu Gln Asp Pro Cys Ser Asn Cys Pro
            20                  25                  30

Ala Gly Thr Phe Cys Asp Asn Asn Arg Asn Gln Ile Cys Ser Pro Cys
        35                  40                  45

Pro Pro Asn Ser Phe Ser Ser Ala Gly Gly Gln Arg Thr Cys Asp Ile
    50                  55                  60

Cys Arg Gln Cys Lys Gly Val Phe Arg Thr Arg Lys Glu Cys Ser Ser
65                  70                  75                  80

Thr Ser Asn Ala Glu Cys Asp Cys Thr Pro Gly Phe His Cys Leu Gly
                85                  90                  95

Ala Gly Cys Ser Met Cys Glu Gln Asp Cys Lys Gln Gly Gln Glu Leu
            100                 105                 110

Thr Lys Lys Gly Cys Lys Asp Cys Cys Phe Gly Thr Phe Asn Asp Gln
        115                 120                 125

Lys Arg Gly Ile Cys Arg Pro Trp Thr Asn Cys Ser Leu Asp Gly Lys
    130                 135                 140

Ser Val Leu Val Asn Gly Thr Lys Glu Arg Asp Val Val Cys Gly Pro
145                 150                 155                 160

Ser Pro Ala Asp Leu Ser Pro Gly Ala Ser Ser Val Thr Pro Pro Ala
                165                 170                 175

Pro Ala Arg Glu Pro Gly His Ser Pro Gln Ile Ile Ser Phe Phe Leu
            180                 185                 190

Ala Leu Thr Ser Thr Ala Leu Leu Phe Leu Leu Phe Phe Leu Thr Leu
        195                 200                 205

Arg Phe Ser Val Val Lys Arg Gly Arg Lys Lys Leu Leu Tyr Ile Phe
    210                 215                 220

Lys Gln Pro Phe Met Arg Pro Val Gln Thr Thr Gln Glu Glu Asp Gly
225                 230                 235                 240

Cys Ser Cys Arg Phe Pro Glu Glu Glu Gly Gly Cys Glu Leu Arg
                245                 250                 255

Val Lys Phe Ser Arg Ser Ala Asp Ala Pro Ala Tyr Gln Gln Gly Gln
            260                 265                 270

Asn Gln Leu Tyr Asn Glu Leu Asn Leu Gly Arg Arg Glu Glu Tyr Asp
        275                 280                 285

Val Leu Asp Lys Arg Arg Gly Arg Asp Pro Glu Met Gly Gly Lys Pro
    290                 295                 300

Gln Arg Arg Lys Asn Pro Gln Glu Gly Leu Tyr Asn Glu Leu Gln Lys
305                 310                 315                 320

Asp Lys Met Ala Glu Ala Tyr Ser Glu Ile Gly Met Lys Gly Glu Arg
                325                 330                 335

Arg Arg Gly Lys Gly His Asp Gly Leu Tyr Gln Gly Leu Ser Thr Ala
            340                 345                 350

Thr Lys Asp Thr Tyr Asp Ala Leu His Met Gln Ala Leu Pro Pro Arg
        355                 360                 365
```

<210> SEQ ID NO 26

```
<211> LENGTH: 152
<212> TYPE: PRT
<213> ORGANISM: Artificial Sequence
<220> FEATURE:
<223> OTHER INFORMATION: CD28 and CD3-zeta endodomains

<400> SEQUENCE: 26

Ser Lys Arg Ser Arg Leu Leu His Ser Asp Tyr Met Asn Met Thr Pro
1               5                   10                  15

Arg Arg Pro Gly Pro Thr Arg Lys His Tyr Gln Pro Tyr Ala Pro Pro
            20                  25                  30

Arg Asp Phe Ala Ala Tyr Arg Ser Arg Val Lys Phe Ser Arg Ser Ala
        35                  40                  45

Asp Ala Pro Ala Tyr Gln Gln Gly Gln Asn Gln Leu Tyr Asn Glu Leu
    50                  55                  60

Asn Leu Gly Arg Arg Glu Glu Tyr Asp Val Leu Asp Lys Arg Arg Gly
65                  70                  75                  80

Arg Asp Pro Glu Met Gly Gly Lys Pro Arg Arg Lys Asn Pro Gln Glu
                85                  90                  95

Gly Leu Tyr Asn Glu Leu Gln Lys Asp Lys Met Ala Glu Ala Tyr Ser
            100                 105                 110

Glu Ile Gly Met Lys Gly Glu Arg Arg Arg Gly Lys Gly His Asp Gly
        115                 120                 125

Leu Tyr Gln Gly Leu Ser Thr Ala Thr Lys Asp Thr Tyr Asp Ala Leu
    130                 135                 140

His Met Gln Ala Leu Pro Pro Arg
145                 150

<210> SEQ ID NO 27
<211> LENGTH: 188
<212> TYPE: PRT
<213> ORGANISM: Artificial Sequence
<220> FEATURE:
<223> OTHER INFORMATION: CD28, OX40 and CD3-zeta endodomains

<400> SEQUENCE: 27

Ser Lys Arg Ser Arg Leu Leu His Ser Asp Tyr Met Asn Met Thr Pro
1               5                   10                  15

Arg Arg Pro Gly Pro Thr Arg Lys His Tyr Gln Pro Tyr Ala Pro Pro
            20                  25                  30

Arg Asp Phe Ala Ala Tyr Arg Ser Arg Asp Gln Arg Leu Pro Pro Asp
        35                  40                  45

Ala His Lys Pro Pro Gly Gly Gly Ser Phe Arg Thr Pro Ile Gln Glu
    50                  55                  60

Glu Gln Ala Asp Ala His Ser Thr Leu Ala Lys Ile Arg Val Lys Phe
65                  70                  75                  80

Ser Arg Ser Ala Asp Ala Pro Ala Tyr Gln Gln Gly Gln Asn Gln Leu
                85                  90                  95

Tyr Asn Glu Leu Asn Leu Gly Arg Arg Glu Glu Tyr Asp Val Leu Asp
            100                 105                 110

Lys Arg Arg Gly Arg Asp Pro Glu Met Gly Gly Lys Pro Arg Arg Lys
        115                 120                 125

Asn Pro Gln Glu Gly Leu Tyr Asn Glu Leu Gln Lys Asp Lys Met Ala
    130                 135                 140

Glu Ala Tyr Ser Glu Ile Gly Met Lys Gly Glu Arg Arg Arg Gly Lys
145                 150                 155                 160

Gly His Asp Gly Leu Tyr Gln Gly Leu Ser Thr Ala Thr Lys Asp Thr
```

```
                  165                 170                 175

Tyr Asp Ala Leu His Met Gln Ala Leu Pro Pro Arg
            180                 185

<210> SEQ ID NO 28
<211> LENGTH: 23
<212> TYPE: PRT
<213> ORGANISM: Artificial Sequence
<220> FEATURE:
<223> OTHER INFORMATION: CD8alpha transmembrane domain

<400> SEQUENCE: 28

Ile Tyr Ile Trp Ala Pro Leu Ala Gly Thr Cys Gly Val Leu Leu Leu
1               5                   10                  15

Ser Leu Val Ile Thr Leu Tyr
            20

<210> SEQ ID NO 29
<211> LENGTH: 5
<212> TYPE: PRT
<213> ORGANISM: Artificial Sequence
<220> FEATURE:
<223> OTHER INFORMATION: linker peptide sequence

<400> SEQUENCE: 29

Ser Gly Gly Gly Gly
1               5

<210> SEQ ID NO 30
<211> LENGTH: 281
<212> TYPE: PRT
<213> ORGANISM: Artificial Sequence
<220> FEATURE:
<223> OTHER INFORMATION: sequence of an engineered pre-T-alpha chain

<400> SEQUENCE: 30

Met Ala Gly Thr Trp Leu Leu Leu Leu Ala Leu Gly Cys Pro Ala
1               5                   10                  15

Leu Pro Thr Gly Val Gly Gly Thr Pro Phe Pro Ser Leu Ala Pro Pro
            20                  25                  30

Ile Met Leu Leu Val Asp Gly Lys Gln Gln Met Val Val Val Cys Leu
        35                  40                  45

Val Leu Asp Val Ala Pro Pro Gly Leu Asp Ser Pro Ile Trp Phe Ser
    50                  55                  60

Ala Gly Asn Gly Ser Ala Leu Asp Ala Phe Thr Tyr Gly Pro Ser Pro
65                  70                  75                  80

Ala Thr Asp Gly Thr Trp Thr Asn Leu Ala His Leu Ser Leu Pro Ser
                85                  90                  95

Glu Glu Leu Ala Ser Trp Glu Pro Leu Val Cys His Thr Gly Pro Gly
            100                 105                 110

Ala Glu Gly His Ser Arg Ser Thr Gln Pro Met His Leu Ser Gly Glu
        115                 120                 125

Ala Ser Thr Ala Arg Thr Cys Pro Gln Glu Pro Leu Arg Gly Thr Pro
    130                 135                 140

Gly Gly Ala Leu Trp Leu Gly Val Leu Arg Leu Leu Phe Lys Leu
145                 150                 155                 160

Leu Leu Phe Asp Leu Leu Leu Thr Cys Ser Cys Leu Cys Asp Pro Ala
                165                 170                 175

Gly Pro Leu Pro Ser Pro Ala Thr Thr Thr Arg Leu Arg Ala Leu Gly
            180                 185                 190
```

Ser His Arg Leu His Pro Ala Thr Glu Thr Gly Gly Arg Glu Ala Thr
    195                 200                 205

Ser Ser Pro Arg Pro Gln Pro Arg Asp Arg Arg Trp Gly Asp Thr Pro
    210                 215                 220

Pro Gly Arg Lys Pro Gly Ser Pro Val Trp Gly Glu Gly Ser Tyr Leu
225                 230                 235                 240

Ser Ser Tyr Pro Thr Cys Pro Ala Gln Ala Trp Cys Ser Arg Ser Ala
            245                 250                 255

Leu Arg Ala Pro Ser Ser Leu Gly Ala Phe Phe Ala Gly Asp Leu
            260                 265                 270

Pro Pro Pro Leu Gln Ala Gly Ala Ala
        275                 280

<210> SEQ ID NO 31
<211> LENGTH: 393
<212> TYPE: PRT
<213> ORGANISM: Artificial Sequence
<220> FEATURE:
<223> OTHER INFORMATION: B2M-L-PreTalpha sequence

<400> SEQUENCE: 31

Met Ser Arg Ser Val Ala Leu Ala Val Leu Ala Leu Leu Ser Leu Ser
1               5                   10                  15

Gly Leu Glu Ala Ile Gln Arg Thr Pro Lys Ile Gln Val Tyr Ser Arg
            20                  25                  30

His Pro Ala Glu Asn Gly Lys Ser Asn Phe Leu Asn Cys Tyr Val Ser
        35                  40                  45

Gly Phe His Pro Ser Asp Ile Glu Val Asp Leu Leu Lys Asn Gly Glu
    50                  55                  60

Arg Ile Glu Lys Val Glu His Ser Asp Leu Ser Phe Ser Lys Asp Trp
65                  70                  75                  80

Ser Phe Tyr Leu Leu Tyr Tyr Thr Glu Phe Thr Pro Thr Glu Lys Asp
                85                  90                  95

Glu Tyr Ala Cys Arg Val Asn His Val Thr Leu Ser Gln Pro Lys Ile
            100                 105                 110

Val Lys Trp Asp Arg Asp Met Ser Gly Gly Gly Ser Gly Gly Gly
        115                 120                 125

Gly Ser Gly Gly Gly Ser Thr Pro Phe Pro Ser Leu Ala Pro Pro
    130                 135                 140

Ile Met Leu Leu Val Asp Gly Lys Gln Gln Met Val Val Val Cys Leu
145                 150                 155                 160

Val Leu Asp Val Ala Pro Pro Gly Leu Asp Ser Pro Ile Trp Phe Ser
                165                 170                 175

Ala Gly Asn Gly Ser Ala Leu Asp Ala Phe Thr Tyr Gly Pro Ser Pro
            180                 185                 190

Ala Thr Asp Gly Thr Trp Thr Asn Leu Ala His Leu Ser Leu Pro Ser
        195                 200                 205

Glu Glu Leu Ala Ser Trp Glu Pro Leu Val Cys His Thr Gly Pro Gly
    210                 215                 220

Ala Glu Gly His Ser Arg Ser Thr Gln Pro Met His Leu Ser Gly Glu
225                 230                 235                 240

Ala Ser Thr Ala Arg Thr Cys Pro Gln Glu Pro Leu Arg Gly Thr Pro
                245                 250                 255

Gly Gly Ala Leu Trp Leu Gly Val Leu Arg Leu Leu Leu Phe Lys Leu
            260                 265                 270

```
Leu Leu Phe Asp Leu Leu Thr Cys Ser Cys Leu Cys Asp Pro Ala
        275                 280                 285

Gly Pro Leu Pro Ser Pro Ala Thr Thr Thr Arg Leu Arg Ala Leu Gly
290                 295                 300

Ser His Arg Leu His Pro Ala Thr Glu Thr Gly Gly Arg Glu Ala Thr
305                 310                 315                 320

Ser Ser Pro Arg Pro Gln Pro Arg Asp Arg Arg Trp Gly Asp Thr Pro
            325                 330                 335

Pro Gly Arg Lys Pro Gly Ser Pro Val Trp Gly Gly Ser Tyr Leu
            340                 345                 350

Ser Ser Tyr Pro Thr Cys Pro Ala Gln Ala Trp Cys Ser Arg Ser Ala
            355                 360                 365

Leu Arg Ala Pro Ser Ser Ser Leu Gly Ala Phe Phe Ala Gly Asp Leu
370                 375                 380

Pro Pro Pro Leu Gln Ala Gly Ala Ala
385                 390

<210> SEQ ID NO 32
<211> LENGTH: 435
<212> TYPE: PRT
<213> ORGANISM: Artificial Sequence
<220> FEATURE:
<223> OTHER INFORMATION: B2M-L-PreTalpha-41BB-Z sequence

<400> SEQUENCE: 32

Met Ser Arg Ser Val Ala Leu Ala Val Leu Ala Leu Leu Ser Leu Ser
1               5                   10                  15

Gly Leu Glu Ala Ile Gln Arg Thr Pro Lys Ile Gln Val Tyr Ser Arg
            20                  25                  30

His Pro Ala Glu Asn Gly Lys Ser Asn Phe Leu Asn Cys Tyr Val Ser
        35                  40                  45

Gly Phe His Pro Ser Asp Ile Glu Val Asp Leu Leu Lys Asn Gly Glu
    50                  55                  60

Arg Ile Glu Lys Val Glu His Ser Asp Leu Ser Phe Ser Lys Asp Trp
65                  70                  75                  80

Ser Phe Tyr Leu Leu Tyr Tyr Thr Glu Phe Thr Pro Thr Glu Lys Asp
                85                  90                  95

Glu Tyr Ala Cys Arg Val Asn His Val Thr Leu Ser Gln Pro Lys Ile
            100                 105                 110

Val Lys Trp Asp Arg Asp Met Ser Gly Gly Gly Gly Ser Gly Gly Gly
        115                 120                 125

Gly Ser Gly Gly Gly Gly Ser Thr Pro Phe Pro Ser Leu Ala Pro Pro
    130                 135                 140

Ile Met Leu Leu Val Asp Gly Lys Gln Gln Met Val Val Val Cys Leu
145                 150                 155                 160

Val Leu Asp Val Ala Pro Pro Gly Leu Asp Ser Pro Ile Trp Phe Ser
                165                 170                 175

Ala Gly Asn Gly Ser Ala Leu Asp Ala Phe Thr Tyr Gly Pro Ser Pro
            180                 185                 190

Ala Thr Asp Gly Thr Trp Thr Asn Leu Ala His Leu Ser Leu Pro Ser
        195                 200                 205

Glu Glu Leu Ala Ser Trp Glu Pro Leu Val Cys His Thr Gly Pro Gly
    210                 215                 220

Ala Glu Gly His Ser Arg Ser Thr Gln Pro Met His Leu Ser Gly Glu
225                 230                 235                 240
```

```
Ala Ser Thr Ala Arg Thr Cys Pro Gln Glu Pro Leu Arg Gly Thr Pro
                245                 250                 255

Gly Gly Ile Ile Ser Phe Phe Leu Ala Leu Thr Ser Thr Ala Leu Leu
            260                 265                 270

Phe Leu Leu Phe Phe Leu Thr Leu Arg Phe Ser Val Val Lys Arg Gly
        275                 280                 285

Arg Lys Lys Leu Leu Tyr Ile Phe Lys Gln Pro Phe Met Arg Pro Val
    290                 295                 300

Gln Thr Thr Gln Glu Glu Asp Gly Cys Ser Cys Arg Phe Pro Glu Glu
305                 310                 315                 320

Glu Glu Arg Val Lys Phe Ser Arg Ser Ala Asp Ala Pro Ala Tyr Gln
                325                 330                 335

Gln Gly Gln Asn Gln Leu Tyr Asn Glu Leu Asn Leu Gly Arg Arg Glu
            340                 345                 350

Glu Tyr Asp Val Leu Asp Lys Arg Arg Gly Arg Asp Pro Glu Met Gly
        355                 360                 365

Gly Lys Pro Gln Arg Arg Lys Asn Pro Gln Glu Gly Leu Tyr Asn Glu
    370                 375                 380

Leu Gln Lys Asp Lys Met Ala Glu Ala Tyr Ser Glu Ile Gly Met Lys
385                 390                 395                 400

Gly Glu Arg Arg Arg Gly Lys Gly His Asp Gly Leu Tyr Gln Gly Leu
                405                 410                 415

Ser Thr Ala Thr Lys Asp Thr Tyr Asp Ala Leu His Met Gln Ala Leu
            420                 425                 430

Pro Pro Arg
        435

<210> SEQ ID NO 33
<211> LENGTH: 7
<212> TYPE: PRT
<213> ORGANISM: Artificial Sequence
<220> FEATURE:
<223> OTHER INFORMATION: Heavy chain complementarity determining region
      (CDR), CDR1

<400> SEQUENCE: 33

Gly Phe Asn Val Lys Asp Thr
1               5

<210> SEQ ID NO 34
<211> LENGTH: 6
<212> TYPE: PRT
<213> ORGANISM: Artificial Sequence
<220> FEATURE:
<223> OTHER INFORMATION: Heavy chain CDR2

<400> SEQUENCE: 34

Asp Pro Ser Asp Gly Asp
1               5

<210> SEQ ID NO 35
<211> LENGTH: 10
<212> TYPE: PRT
<213> ORGANISM: Artificial Sequence
<220> FEATURE:
<223> OTHER INFORMATION: Heavy chain CDR3

<400> SEQUENCE: 35

Trp Phe Gly Asp Tyr Gly Ala Met Asn Tyr
1               5                   10
```

<210> SEQ ID NO 36
<211> LENGTH: 11
<212> TYPE: PRT
<213> ORGANISM: Artificial Sequence
<220> FEATURE:
<223> OTHER INFORMATION: Light chain CDR1

<400> SEQUENCE: 36

Leu Ala Ser Gln Thr Ile Gly Thr Trp Leu Ala
1               5                   10

<210> SEQ ID NO 37
<211> LENGTH: 7
<212> TYPE: PRT
<213> ORGANISM: Artificial Sequence
<220> FEATURE:
<223> OTHER INFORMATION: Light chain CDR2

<400> SEQUENCE: 37

Ala Ala Thr Ser Leu Ala Asp
1               5

<210> SEQ ID NO 38
<211> LENGTH: 9
<212> TYPE: PRT
<213> ORGANISM: Artificial Sequence
<220> FEATURE:
<223> OTHER INFORMATION: Light chain CDR3

<400> SEQUENCE: 38

Gln Gln Leu Tyr Ser Lys Pro Tyr Thr
1               5

<210> SEQ ID NO 39
<211> LENGTH: 245
<212> TYPE: PRT
<213> ORGANISM: Artificial Sequence
<220> FEATURE:
<223> OTHER INFORMATION: scFV generated from the BB7.7 hybridoma (first
      binding domain)

<400> SEQUENCE: 39

Gln Val Gln Leu Gln Gln Ser Gly Ala Glu Leu Ala Arg Pro Gly Ala
1               5                   10                  15

Ser Val Lys Leu Ser Cys Lys Ala Ser Gly Tyr Thr Phe Thr Ser His
                20                  25                  30

Trp Met Gln Trp Val Arg Gln Arg Pro Gly Gln Gly Leu Glu Trp Ile
            35                  40                  45

Gly Thr Ile Tyr Pro Gly Asp Gly Asp Thr Arg Tyr Thr Gln Asn Phe
        50                  55                  60

Lys Gly Lys Ala Thr Leu Thr Ala Asp Lys Ser Ser Thr Thr Ala Tyr
65                  70                  75                  80

Leu His Leu Ser Ser Leu Ser Ser Glu Asp Ser Ala Val Tyr Tyr Cys
                85                  90                  95

Ala Arg Asp Glu Ile Thr Thr Val Val Pro Arg Gly Phe Ala Tyr Trp
            100                 105                 110

Gly Gln Gly Thr Ser Val Thr Val Ser Ser Gly Gly Gly Ser Gly
            115                 120                 125

Gly Gly Gly Ser Gly Gly Gly Ser Glu Leu Val Leu Thr Gln Thr
        130                 135                 140

Pro Ser Ser Leu Ser Ala Ser Leu Gly Asp Arg Val Thr Ile Ser Cys

```
                145                 150                 155                 160
Arg Ala Ser Gln Asp Ile Ser Ser Tyr Leu Asn Trp Tyr Gln Gln Lys
                    165                 170                 175

Pro Asp Gly Thr Ile Lys Leu Leu Ile Tyr Tyr Thr Ser Arg Leu Tyr
                180                 185                 190

Ser Gly Val Pro Pro Arg Phe Ser Gly Ser Gly Ala Gly Thr Asp Tyr
            195                 200                 205

Ser Leu Thr Ile Ser Asn Leu Glu Gln Glu Asp Ile Ala Thr Tyr Phe
        210                 215                 220

Cys Gln Gln Gly Asn Val Ile Pro Tyr Thr Phe Gly Gly Gly Thr Lys
225                 230                 235                 240

Leu Glu Met Lys Arg
                245

<210> SEQ ID NO 40
<211> LENGTH: 245
<212> TYPE: PRT
<213> ORGANISM: Artificial Sequence
<220> FEATURE:
<223> OTHER INFORMATION: scFV generated from the BB7.7 hybridoma (first
      binding domain)

<400> SEQUENCE: 40

Gln Val Gln Leu Gln Gln Ser Gly Ala Glu Leu Thr Arg Pro Gly Ala
1               5                   10                  15

Ser Val Lys Leu Ser Cys Lys Ala Ser Gly Tyr Thr Phe Thr Ser His
            20                  25                  30

Trp Met Gln Trp Val Arg Gln Arg Pro Gly Gln Gly Leu Glu Trp Ile
        35                  40                  45

Gly Thr Ile Tyr Pro Gly Asp Gly Asp Thr Arg Tyr Thr Gln Asn Phe
    50                  55                  60

Lys Gly Lys Ala Thr Leu Thr Ala Asp Lys Ser Ser Thr Thr Ala Tyr
65                  70                  75                  80

Leu His Leu Ser Ser Leu Ser Ser Glu Asp Ser Ala Val Tyr Tyr Cys
                85                  90                  95

Ala Arg Asp Glu Ile Thr Thr Val Val Pro Arg Gly Phe Ala Tyr Trp
            100                 105                 110

Gly Gln Gly Thr Leu Val Thr Val Ser Ser Gly Gly Gly Gly Ser Gly
        115                 120                 125

Gly Gly Gly Ser Gly Gly Gly Ser Glu Leu Val Leu Thr Gln Ser
    130                 135                 140

Pro Ser Ser Leu Ser Ala Ser Leu Gly Asp Thr Ile Thr Ile Thr Cys
145                 150                 155                 160

His Ala Ser Gln Asn Ile Asn Val Trp Leu Ser Trp Tyr Gln Gln Lys
                165                 170                 175

Pro Gly Asn Ile Pro Gln Leu Leu Ile Tyr Lys Ala Ser Asn Leu His
            180                 185                 190

Thr Gly Val Pro Ser Arg Phe Ser Gly Arg Gly Ser Gly Thr Gly Phe
        195                 200                 205

Thr Leu Thr Ile Ser Ser Leu Gln Pro Glu Asp Ile Gly Thr Tyr Tyr
    210                 215                 220

Cys Gln Gln Gly Gln Ser Tyr Pro Leu Thr Phe Gly Gly Gly Thr Lys
225                 230                 235                 240

Leu Glu Met Lys Arg
                245
```

```
<210> SEQ ID NO 41
<211> LENGTH: 244
<212> TYPE: PRT
<213> ORGANISM: Artificial Sequence
<220> FEATURE:
<223> OTHER INFORMATION: scFV comprising the CDR sequences from OKT3

<400> SEQUENCE: 41

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Val Ser Tyr Met
            20                  25                  30

Asn Trp Tyr Gln Gln Lys Ser Gly Thr Ser Pro Lys Arg Trp Ile Tyr
            35                  40                  45

Asp Thr Ser Lys Leu Ala Ser Gly Val Pro Ala His Phe Arg Gly Ser
    50                  55                  60

Gly Ser Gly Thr Ser Tyr Ser Leu Thr Ile Ser Gly Met Glu Ala Glu
65                  70                  75                  80

Asp Ala Ala Thr Tyr Tyr Cys Gln Gln Trp Ser Ser Asn Pro Phe Thr
                85                  90                  95

Phe Gly Ser Gly Thr Lys Leu Glu Ile Asn Arg Ser Ser Ser Gly Gly
            100                 105                 110

Gly Gly Ser Gly Gly Gly Gly Ser Gly Gly Gly Ser Gln Val Gln
            115                 120                 125

Leu Gln Gln Ser Gly Ala Glu Leu Ala Arg Pro Gly Ala Ser Val Lys
130                 135                 140

Met Ser Cys Lys Ala Ser Gly Tyr Thr Phe Thr Arg Tyr Thr Met His
145                 150                 155                 160

Trp Val Lys Gln Arg Pro Gly Gln Gly Leu Glu Trp Ile Gly Tyr Ile
                165                 170                 175

Asn Pro Ser Arg Gly Tyr Thr Asn Tyr Asn Gln Lys Phe Lys Asp Lys
            180                 185                 190

Ala Thr Leu Thr Thr Asp Lys Ser Ser Ser Thr Ala Tyr Met Gln Leu
        195                 200                 205

Ser Ser Leu Thr Ser Glu Asp Ser Ala Val Tyr Tyr Cys Ala Arg Tyr
    210                 215                 220

Tyr Asp Asp His Tyr Cys Leu Asp Tyr Trp Gly Gln Gly Thr Thr Leu
225                 230                 235                 240

Thr Val Ser Ser

<210> SEQ ID NO 42
<211> LENGTH: 5
<212> TYPE: PRT
<213> ORGANISM: Artificial Sequence
<220> FEATURE:
<223> OTHER INFORMATION: peptide linker

<400> SEQUENCE: 42

Gly Gly Gly Gly Ser
1               5

<210> SEQ ID NO 43
<211> LENGTH: 4
<212> TYPE: PRT
<213> ORGANISM: Artificial Sequence
<220> FEATURE:
<223> OTHER INFORMATION: ITAM (immunoreceptor tyrosine-based activation
      motif)
<220> FEATURE:
```

```
<221> NAME/KEY: misc_feature
<222> LOCATION: (2)..(3)
<223> OTHER INFORMATION: Xaa can be any naturally occurring amino acid
<220> FEATURE:
<221> NAME/KEY: MISC_FEATURE
<222> LOCATION: (4)..(4)
<223> OTHER INFORMATION: Xaa may be Leu or Ile

<400> SEQUENCE: 43

Tyr Xaa Xaa Xaa
1

<210> SEQ ID NO 44
<211> LENGTH: 4
<212> TYPE: PRT
<213> ORGANISM: Artificial Sequence
<220> FEATURE:
<223> OTHER INFORMATION: basic amino acid furin target sequence
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: MISC_FEATURE
<222> LOCATION: (3)..(3)
<223> OTHER INFORMATION: Xaa may be Arg or Lys

<400> SEQUENCE: 44

Arg Xaa Xaa Arg
1

<210> SEQ ID NO 45
<211> LENGTH: 7
<212> TYPE: PRT
<213> ORGANISM: Artificial Sequence
<220> FEATURE:
<223> OTHER INFORMATION: consensus Tobacco Etch Virus (TEV) cleavage
      site

<400> SEQUENCE: 45

Glu Asn Leu Tyr Phe Gln Ser
1               5
```

UNITED STATES PATENT AND TRADEMARK OFFICE
CERTIFICATE OF CORRECTION

PATENT NO. : 11,643,453 B2
APPLICATION NO. : 16/754673
DATED : May 9, 2023
INVENTOR(S) : Martin Pulé et al.

Page 1 of 1

It is certified that error appears in the above-identified patent and that said Letters Patent is hereby corrected as shown below:

On the Title Page

At item (57), Line 1, "comprises;" should be -- comprises: --.

Signed and Sealed this
Fifth Day of December, 2023

Katherine Kelly Vidal
*Director of the United States Patent and Trademark Office*